United States Patent
Cerretti

(10) Patent No.: US 7,399,832 B2
(45) Date of Patent: *Jul. 15, 2008

(54) METALLOPROTEASE-DISINTEGRIN ADAM23 (SVPH3-17)

(75) Inventor: Douglas P. Cerretti, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/642,458

(22) Filed: Dec. 19, 2006

(65) Prior Publication Data

US 2007/0087412 A1    Apr. 19, 2007

Related U.S. Application Data

(60) Division of application No. 10/202,675, filed on Jul. 23, 2002, now Pat. No. 7,196,168, which is a division of application No. 09/634,252, filed on Aug. 7, 2000, now Pat. No. 6,787,644, which is a continuation of application No. PCT/US99/03016, filed on Feb. 11, 1999.

(60) Provisional application No. 60/074,310, filed on Feb. 11, 1998.

(51) Int. Cl.
*C07K 14/435* (2006.01)
*C07K 19/00* (2006.01)
*C12N 15/12* (2006.01)
*C12N 15/62* (2006.01)
*C12N 15/79* (2006.01)

(52) U.S. Cl. ............... 530/350; 435/69.1; 435/69.7; 435/252.3; 435/320.1; 536/23.1; 536/23.4

(58) Field of Classification Search .............. None
See application file for complete search history.

(56) References Cited

U.S. PATENT DOCUMENTS

| | | | |
|---|---|---|---|
| 5,449,758 A | 9/1995 | Hartley | |
| 5,552,526 A | 9/1996 | Nakamura et al. | |
| 5,631,351 A | 5/1997 | Nakamura et al. | |
| 5,705,341 A | 1/1998 | Nakamura et al. | |
| 6,265,199 B1 | 7/2001 | Sheppard et al. | |
| 6,787,644 B1 * | 9/2004 | Cerretti | 536/23.2 |
| 7,074,408 B2 * | 7/2006 | Fanslow et al. | 424/185.1 |
| 7,196,168 B2 * | 3/2007 | Cerretti | 530/350 |
| 2002/0001840 A1 | 1/2002 | Lopez-Otin et al. | |
| 2002/0072102 A1 | 6/2002 | Sheppard et al. | |

FOREIGN PATENT DOCUMENTS

| | | |
|---|---|---|
| EP | 0 633 268 A2 | 1/1995 |
| WO | WO 00/02912 A2 | 1/2000 |

OTHER PUBLICATIONS

Katagiri et al., *Cytogenetic Cell Genetics*, 68: 39-44 (1995).
EMB/GENBANK Databases Accession No. AA050162 Sequence Reference MMAA50162, 1996, "The WashU-HHMI Mouse EST Project", XP002107448.
EMB/GENBANK Databases Accession No. W75581 Sequence Reference MM58129, 1996, "The WashU-HHMI Mouse EST Project", XP002107449.
Scopes, R., "Protein purification", Springer Verlag, New York, (1987), pp. 284-289.
Sagane, K. et al., *Biochemical Journal* 334 (Pt.1): 93-98, (1998).
Black et al., *Current Opinion in Cell Biology*, 10: 654-659 (1998).
Gilpin, B.J. et al., 1998, "A novel, secreted form of human ADAM 12 (meltrin alpha) provokes myogenesis in vivo", *The Journal of Biological Chemistry*, vol. 273, pp. 157-166.
GenBank databases Accession No. AA718688, 1997, Marra et al., "The WashU-HHMI Mouse EST Project."
GenBank databases Accession No. F08148, 1995, Auffray et al., *Sciences de la Vie*, vol. 318, pp. 263-272.
GenBank databases Accession No. AA511039, 1997, Marra et al., "The WashU-HHMI Mouse EST Project."
GenBank databases Accession No. R52569, 1995, Hillier et al., "The WashU-Merck EST Project."
GenBank Accession No. R15038, Hillier et al., "The WashU-Merck EST Project", Apr. 13, 1995.
Jia, L.-G., et al. 1997, "Function of Disintegrin-like/Cysteine-rich comains of Atrolysin A", The Journal of Biological Chemistry, vol. 272, pp. 13094-13102.

* cited by examiner

*Primary Examiner*—Nashaat T. Nashed
*Assistant Examiner*—William W. Moore
(74) *Attorney, Agent, or Firm*—Nathan A. Machin

(57) ABSTRACT

The invention is directed to purified and isolated novel SVPH3-13 or SVPH3-17 polypeptides, the nucleic acids encoding such polypeptides, processes for production of recombinant forms of such polypeptides, antibodies generated against these polypeptides, fragmented peptides derived from these polypeptides, and the uses of the above.

5 Claims, 2 Drawing Sheets

SEQUENCE LISTING

<160> NUMBER OF SEQ ID NOS: 10

<210> SEQ ID NO 1
<211> LENGTH: 58
<212> TYPE: DNA
<213> ORGANISM: Homo sapiens

<400> SEQUENCE: 1

```
cttcttgatc ctcctgagtg tggcaatggc ttcattgaaa ctggagagga gtgtgatt      58
```

<210> SEQ ID NO 2
<211> LENGTH: 2499
<212> TYPE: DNA
<213> ORGANISM: Homo sapiens

<400> SEQUENCE: 2

```
atgaagccgc ccggcagcag ctcgcggcag ccgcccctgg cgggctgcag ccttgccggc       60
gcttcctgcg gcccccaacg cggccccgcc ggctcggtgc ctgccagcgc cccggcccgc      120
acgccgccct gccgcctgct tctcgtcctt ctcctgctgc ctccgctcgc cgcctcgtcc      180
cggccccgcg cctgggggc tgctgcgccc agcgctccgc attggaatga aactgcagaa       240
aaaaatttgg gagtcctggc agatgaagac aatacattgc aacagaatag cagcagtaat      300
atcagttaca gcaatgcaat gcagaaagaa atcacactgc cttcaagact catatattac      360
atcaaccaag actcggaaag cccttatcac gttcttgaca caaaggcaag acaccagcaa      420
aaacataata aggctgtcca tctgcccag gcaagcttcc agattgaagc cttcggctcc       480
aaattcattc ttgacctcat actgaacaat ggtttgttgt cttctgatta tgtggagatt      540
cactacgaaa atgggaaacc acagtactct aagggtggag agcactgtta ctaccatgga      600
agcatcagag gcgtcaaaga ctccaaggtg gctctgtcaa cctgcaatgg acttcatggc      660
atgtttgaag atgataccct cgtgtatatg atagagccac tagagctggt tcatgatgag      720
aaaagcacag gtcgaccaca tataatccag aaaaccttgg caggacagta ttctaagcaa      780
atgaagaatc tcactatgga aagaggtgac cagtggccct ttctctctga attacagtgg      840
ttgaaaagaa ggaagagagc agtgaatcca tcacgtggta tatttgaaga aatgaaatat      900
ttggaactta tgattgttaa tgatcacaaa acgtataaga agcatcgctc ttctcatgca      960
cataccaaca actttgcaaa gtccgtggtc aaccttgtgg attctatta caaggagcag     1020 ctcaacacca gggttgtcct ggtggctgta gagacctgga ctgagaagga tcagattgac     1080
atcaccacca accctgtgca gatgctccat gagttctcaa aataccggca gcgcattaag     1140
cagcatgctg atgctgtgca cctcatctcg cgggtgacat ttcactataa gagaagcagt    1200
ctgagttact ttggaggtgt ctgttctcgc acaagaggag ttggtgtgaa tgagtatggt    1260
```

-continued

```
cttccaatgg cagtggcaca agtattatcg cagagcctgg ctcaaaacct tggaatccaa      1320
tgggaacctt ctagcagaaa gccaaaatgt gactgcacag atcctgggg tggctgcatc      1380 atggaggaaa cagggtgtc ccattctcga aaattttcaa agtgcagcat tttggagtat      1440 agagacttt tacagagagg aggtggagcc tgccttttca acaggccaac aaagctattt      1500
gagcccacgg aatgtggaaa tggatacgtg aagctgggg aggagtgtga ttgtggtttt      1560
catgtggaat gctatggatt atgctgtaag aaatgttccc tctccaacgg ggctcactgc      1620
agcgacgggc cctgctgtaa caatacctca tgtcttttc agccacgagg gtatgaatgc      1680
cgggatgctg tgaacgagtg tgatattact gaatattgta ctggagactc tggtcagtgc      1740
ccaccaaatc ttcataagca agacggatat gcatgcaatc aaaatcaggg ccgctgctac      1800
aatggcgagt gcaagaccag agacaaccag tgtcagtaca tctggggaac aaaggctgca      1860
gggtctgaca agttctgcta tgaaaagctg aatacagaag gcactgagaa gggaaactgc      1920
gggaaggatg gagaccggtg gattcagtgc agcaaacatg atgtgttctg tggattctta      1980
ctctgtacca atcttactcg agctccacgt attggtcaac ttcagggtga gatcattcca      2040
acttccttct accatcaagg ccgggtgatt gactgcagtg gtgcccatgt agttttagat      2100
gatgatacgg atgtgggcta tgtagaagat ggaacgccat gtggcccgtc tatgatgtgt      2160
ttagatcgga agtgcctaca aattcaagcc ctaaatatga gcagctgtcc actcgattcc      2220
aagggtaaag tctgttcggg ccatgggtg tgtagtaatg aagccacctg catttgtgat      2280
ttcacctggg cagggacaga ttgcagtatc cgggatccag ttaggaacct tcacccccccc      2340 aaggatgaag acccaaggg tcctagtgcc accaatctca taataggctc atcgctggt      2400 gccatcctgg tagcagctat tgtccttggg ggcacaggct ggggatttaa aaatgtcaag      2460
aagagaaggt tcgatcctac tcagcaaggc cccatctga                            2499
```

<210> SEQ ID NO 3
<211> LENGTH: 20
<212> TYPE: PRT
<213> ORGANISM: Homo sapiens

<400> SEQUENCE: 3

Leu Leu Asp Pro Pro Glu Cys Gly Asn Gly Phe Ile Glu Thr Gly Glu
 1               5                  10                  15

Glu Cys Asp Cys
            20

<210> SEQ ID NO 4
<211> LENGTH: 832
<212> TYPE: PRT
<213> ORGANISM: Homo sapiens

<400> SEQUENCE: 4

Met Lys Pro Pro Gly Ser Ser Arg Gln Pro Leu Ala Gly Cys
 1               5                  10                  15

Ser Leu Ala Gly Ala Ser Cys Gly Pro Gln Arg Gly Pro Ala Gly Ser
                20                  25                  30

Val Pro Ala Ser Ala Pro Ala Arg Thr Pro Pro Cys Arg Leu Leu Leu
            35                  40                  45

Val Leu Leu Leu Pro Pro Leu Ala Ala Ser Ser Arg Pro Arg Ala
        50                  55                  60

Trp Gly Ala Ala Ala Pro Ser Ala Pro His Trp Asn Glu Thr Ala Glu
    65                  70                  75                  80

```
Lys Asn Leu Gly Val Leu Ala Asp Glu Asp Asn Thr Leu Gln Gln Asn
                85                  90                  95

Ser Ser Ser Asn Ile Ser Tyr Ser Asn Ala Met Gln Lys Glu Ile Thr
            100                 105                 110

Leu Pro Ser Arg Leu Ile Tyr Tyr Ile Asn Gln Asp Ser Glu Ser Pro
            115                 120                 125

Tyr His Val Leu Asp Thr Lys Ala Arg His Gln Lys His Asn Lys
    130                 135                 140

Ala Val His Leu Ala Gln Ala Ser Phe Gln Ile Glu Ala Phe Gly Ser
145                 150                 155                 160

Lys Phe Ile Leu Asp Leu Ile Leu Asn Asn Gly Leu Leu Ser Ser Asp
                165                 170                 175

Tyr Val Glu Ile His Tyr Glu Asn Gly Lys Pro Gln Tyr Ser Lys Gly
            180                 185                 190

Gly Glu His Cys Tyr Tyr His Gly Ser Ile Arg Gly Val Lys Asp Ser
        195                 200                 205

Lys Val Ala Leu Ser Thr Cys Asn Gly Leu His Gly Met Phe Glu Asp
210                 215                 220

Asp Thr Phe Val Tyr Met Ile Glu Pro Leu Glu Leu Val His Asp Glu
225                 230                 235                 240

Lys Ser Thr Gly Arg Pro His Ile Ile Gln Lys Thr Leu Ala Gly Gln
                245                 250                 255

Tyr Ser Lys Gln Met Lys Asn Leu Thr Met Glu Arg Gly Asp Gln Trp
            260                 265                 270

Pro Phe Leu Ser Glu Leu Gln Trp Leu Lys Arg Arg Lys Arg Ala Val
        275                 280                 285

Asn Pro Ser Arg Gly Ile Phe Glu Glu Met Lys Tyr Leu Glu Leu Met
    290                 295                 300

Ile Val Asn Asp His Lys Thr Tyr Lys Lys His Arg Ser Ser His Ala
305                 310                 315                 320

His Thr Asn Asn Phe Ala Lys Ser Val Val Asn Leu Val Asp Ser Ile
                325                 330                 335

Tyr Lys Glu Gln Leu Asn Thr Arg Val Val Leu Val Ala Val Glu Thr
            340                 345                 350

Trp Thr Glu Lys Asp Gln Ile Asp Ile Thr Thr Asn Pro Val Gln Met
        355                 360                 365

Leu His Glu Phe Ser Lys Tyr Arg Gln Arg Ile Lys Gln His Ala Asp
    370                 375                 380

Ala Val His Leu Ile Ser Arg Val Thr Phe His Tyr Lys Arg Ser Ser
385                 390                 395                 400

Leu Ser Tyr Phe Gly Gly Val Cys Ser Arg Thr Arg Gly Val Gly Val
                405                 410                 415

Asn Glu Tyr Gly Leu Pro Met Ala Val Ala Gln Val Leu Ser Gln Ser
            420                 425                 430

Leu Ala Gln Asn Leu Gly Ile Gln Trp Glu Pro Ser Ser Arg Lys Pro
        435                 440                 445

Lys Cys Asp Cys Thr Glu Ser Trp Gly Gly Cys Ile Met Glu Glu Thr
    450                 455                 460

Gly Val Ser His Ser Arg Lys Phe Ser Lys Cys Ser Ile Leu Glu Tyr
465                 470                 475                 480

Arg Asp Phe Leu Gln Arg Gly Gly Gly Ala Cys Leu Phe Asn Arg Pro
                485                 490                 495
```

```
Thr Lys Leu Phe Glu Pro Thr Glu Cys Gly Asn Gly Tyr Val Glu Ala
        500                 505                 510
Gly Glu Glu Cys Asp Cys Gly Phe His Val Glu Cys Tyr Gly Leu Cys
        515                 520                 525
Cys Lys Lys Cys Ser Leu Ser Asn Gly Ala His Cys Ser Asp Gly Pro
        530                 535                 540
Cys Cys Asn Asn Thr Ser Cys Leu Phe Gln Pro Arg Gly Tyr Glu Cys
545                 550                 555                 560
Arg Asp Ala Val Asn Glu Cys Asp Ile Thr Glu Tyr Cys Thr Gly Asp
                565                 570                 575
Ser Gly Gln Cys Pro Pro Asn Leu His Lys Gln Asp Gly Tyr Ala Cys
        580                 585                 590
Asn Gln Asn Gln Gly Arg Cys Tyr Asn Gly Glu Cys Lys Thr Arg Asp
        595                 600                 605
Asn Gln Cys Gln Tyr Ile Trp Gly Thr Lys Ala Ala Gly Ser Asp Lys
        610                 615                 620
Phe Cys Tyr Glu Lys Leu Asn Thr Glu Gly Thr Glu Lys Gly Asn Cys
625                 630                 635                 640
Gly Lys Asp Gly Asp Arg Trp Ile Gln Cys Ser Lys His Asp Val Phe
                645                 650                 655
Cys Gly Phe Leu Leu Cys Thr Asn Leu Thr Arg Ala Pro Arg Ile Gly
        660                 665                 670
Gln Leu Gln Gly Glu Ile Ile Pro Thr Ser Phe Tyr His Gln Gly Arg
        675                 680                 685
Val Ile Asp Cys Ser Gly Ala His Val Val Leu Asp Asp Thr Asp
        690                 695                 700
Val Gly Tyr Val Glu Asp Gly Thr Pro Cys Gly Pro Ser Met Met Cys
705                 710                 715                 720
Leu Asp Arg Lys Cys Leu Gln Ile Gln Ala Leu Asn Met Ser Ser Cys
                725                 730                 735
Pro Leu Asp Ser Lys Gly Lys Val Cys Ser Gly His Gly Val Cys Ser
        740                 745                 750
Asn Glu Ala Thr Cys Ile Cys Asp Phe Thr Trp Ala Gly Thr Asp Cys
        755                 760                 765
Ser Ile Arg Asp Pro Val Arg Asn Leu His Pro Pro Lys Asp Glu Gly
        770                 775                 780
Pro Lys Gly Pro Ser Ala Thr Asn Leu Ile Ile Gly Ser Ile Ala Gly
785                 790                 795                 800
Ala Ile Leu Val Ala Ala Ile Val Leu Gly Gly Thr Gly Trp Gly Phe
                805                 810                 815
Lys Asn Val Lys Lys Arg Arg Phe Asp Pro Thr Gln Gln Gly Pro Ile
        820                 825                 830

<210> SEQ ID NO 5
<211> LENGTH: 2604
<212> TYPE: DNA
<213> ORGANISM: Homo sapiens

<400> SEQUENCE: 5
aaggaaaacc gcttcgtgga gcgccagagc atcgtgccac tgcgcctcat ctaccgctcg    60
ggcggcgaag acgaaagtcg gcacgacgcg ctcgacacgc gggtgcgggg cgacctcggt   120
ggccggcagt tgactcatgt tgaccaagca agcttccagg ttgatgcctt ggaacgtca    180 ttcattctcg atgtcgtgct aaatcatgat ttgctgtcct ctgaatacat agagagacac   240
```

```
attgaacatg gaggcaagac tgtggaagtt aaaggaggag agcactgtta ctaccagggc      300
catatccgag gaaaccctga ctcatttgtt gcattgtcaa catgccacgg acttcatggg      360
atgttctatg acgggaacca cacatatctc attgagccag aagaaaatga cactactcaa      420
gaggatttcc attttcattc agtttacaaa tccagactgt ttgaattttc cttggatgat      480
cttccatctg aatttcagca agtaaacatt actccatcaa aatttatttt gaagccaaga      540
ccaaaaagga gtaaacggca gcttcgtcga tatcctcgta atgtagaaga agaaaccaaa      600
tacattgaac tgatgattgt gaatgatcac cttatgttta aaaaacatcg gctttccgtt      660
gtacatacca ataccctatgc gaaatctgtg gtgaacatgg cagatttaat atataaagac      720
caacttaaga ccaggatagt attggttgct atggaaacct gggcgactga caacaagttt      780
gccatatctg aaaatccatt gatcacccta cgtgagttta tgaaatacag agggattttt      840
atcaaagaga aaagtgatgc agttcacctt ttttcgggaa gtcaatttga gagtagccgg      900
agcggggcag cttatattgg tgggatttgc tcgttgctga aggaggagg cgtgaatgaa      960 tttgggaaaa ctgatttaat ggctgttaca cttgcccagt cattagccca taatattggt      1020
attatctcag acaaaagaaa gttagcaagt ggtgaatgta atgcgagga cacgtggtcc      1080 gggtgcataa tgggagacac tggctattat cttcctaaaa agttcaccca gtgtaatatt      1140
gaagagtatc atgacttcct gaatagtgga ggtggtgcct gccttttcaa caaaccttct      1200
aagcttcttg atcctcctga gtgtggcaat ggcttcattg aaactggaga ggagtgtgat      1260 tgtgaaccc cggccgaatg tgtccttgaa ggagcagagt gttgtaagaa atgcaccttg      1320
actcaagact ctcaatgcag tgacggtctt tgctgtaaaa agtgcaagtt tcagcctatg      1380
ggcactgtgt gccgagaagc agtaaatgat tgtgatattc gtgaaacgtg ctcaggaaat      1440
tcaagccagt gtgcccctaa tattcataaa atggatggat attcatgtga tggtgttcag      1500
ggaatttgct ttggaggaag atgcaaaacc agagatagca aatgcaaata catttggggg      1560
caaaaggtga cagcatcaga caaatattgc tatgagaaac tgaatattga agggacggag      1620
aagggtaact gtgggaaaga caagacaca tggatacagt gcaacaaacg ggatgtgctt      1680
tgtggttacc ttttgtgtac caatattggc aatatcccaa ggcttggaga actcgatggt      1740
gaaatcacat ctactttagt tgtgcagcaa ggaagaacat aaactgcag tggtgggcat      1800 gttaagcttg aagaagatgt agatcttggc tatgtggaag atgggacacc ttgtggtccc      1860
caaatgatgt gcttagaaca caggtgtctt cctgtggctt cttttcaactt tagtacttgc      1920 ttgagcagta agaaggcac tatttgctca ggaaatggag tttgcagtaa tgagctgaag      1980
tgtgtgtgta acagacactg gataggttct gattgcaaca cttacttccc tcacaatgat      2040
gatgcaaaga ctggtatcac tctgtctggc aatggtgttg ctggccaccaa tatcataata      2100 ggcataattg ctggcaccat tttagtgctg gccctcatat taggaataac tgcgtggggt      2160
tataaaaact atcgagaaca gagacagtta ccccagggag attatgtaaa aaagcctgga      2220
gatggtgact ttttttatag cgacattcct cccggagtca gcacaaactc agcatctagt      2280
tctaagaaga ggtcaaatgg gctctctcat tcttggagtg aaaggattcc agacacaaaa      2340
catatttcag acatctgtga aaatgggcga cctcgaagta actcttggca aggtaacctg      2400
ggaggcaaca aaaagaaaat cagaggcaaa agatttagac ctcggtctaa ttcaactgag      2460
actttatctc ctgccaagtc tccttcttca tcaactgggt ctattgcctc cagcagaaaa      2520
tacccttacc caatgcctcc acttcctgat gaggacaaga agtgaaccg acaaagtgcc      2580 aggctatggg agacatccat ttaa                                            2604
```

<210> SEQ ID NO 6
<211> LENGTH: 867
<212> TYPE: PRT
<213> ORGANISM: Homo sapiens

<400> SEQUENCE: 6

```
Lys Glu Asn Arg Phe Val Glu Arg Gln Ser Ile Val Pro Leu Arg Leu
  1               5                  10                  15

Ile Tyr Arg Ser Gly Gly Glu Asp Ser Arg His Asp Ala Leu Asp
                 20                  25                  30

Thr Arg Val Arg Gly Asp Leu Gly Arg Gln Leu Thr His Val Asp
             35                  40                  45

Gln Ala Ser Phe Gln Val Asp Ala Phe Gly Thr Ser Phe Ile Leu Asp
 50                  55                  60

Val Val Leu Asn His Asp Leu Leu Ser Glu Tyr Ile Glu Arg His
 65                  70                  75                  80

Ile Glu His Gly Gly Lys Thr Val Glu Val Lys Gly Gly Glu His Cys
                 85                  90                  95

Tyr Tyr Gln Gly His Ile Arg Gly Asn Pro Asp Ser Phe Val Ala Leu
                100                 105                 110

Ser Thr Cys His Gly Leu His Gly Met Phe Tyr Asp Gly Asn His Thr
            115                 120                 125

Tyr Leu Ile Glu Pro Glu Glu Asn Asp Thr Thr Gln Glu Asp Phe His
        130                 135                 140

Phe His Ser Val Tyr Lys Ser Arg Leu Phe Glu Phe Ser Leu Asp Asp
145                 150                 155                 160

Leu Pro Ser Glu Phe Gln Gln Val Asn Ile Thr Pro Ser Lys Phe Ile
                165                 170                 175

Leu Lys Pro Arg Pro Lys Arg Ser Lys Arg Gln Leu Arg Arg Tyr Pro
            180                 185                 190

Arg Asn Val Glu Glu Glu Thr Lys Tyr Ile Glu Leu Met Ile Val Asn
        195                 200                 205

Asp His Leu Met Phe Lys Lys His Arg Leu Ser Val Val His Thr Asn
    210                 215                 220

Thr Tyr Ala Lys Ser Val Val Asn Met Ala Asp Leu Ile Tyr Lys Asp
225                 230                 235                 240

Gln Leu Lys Thr Arg Ile Val Leu Val Ala Met Glu Thr Trp Ala Thr
                245                 250                 255

Asp Asn Lys Phe Ala Ile Ser Glu Asn Pro Leu Ile Thr Leu Arg Glu
            260                 265                 270

Phe Met Lys Tyr Arg Arg Asp Phe Ile Lys Glu Lys Ser Asp Ala Val
        275                 280                 285

His Leu Phe Ser Gly Ser Gln Phe Glu Ser Ser Arg Ser Gly Ala Ala
    290                 295                 300

Tyr Ile Gly Gly Ile Cys Ser Leu Leu Lys Gly Gly Val Asn Glu
305                 310                 315                 320

Phe Gly Lys Thr Asp Leu Met Ala Val Thr Leu Ala Gln Ser Leu Ala
                325                 330                 335

His Asn Ile Gly Ile Ile Ser Asp Lys Arg Lys Leu Ala Ser Gly Glu
            340                 345                 350

Cys Lys Cys Glu Asp Thr Trp Ser Gly Cys Ile Met Gly Asp Thr Gly
        355                 360                 365

Tyr Tyr Leu Pro Lys Lys Phe Thr Gln Cys Asn Ile Glu Glu Tyr His
```

-continued

```
        370             375             380
Asp Phe Leu Asn Ser Gly Gly Ala Cys Leu Phe Asn Lys Pro Ser
385                 390                 395                 400

Lys Leu Leu Asp Pro Pro Glu Cys Gly Asn Gly Phe Ile Glu Thr Gly
                405                 410                 415

Glu Glu Cys Asp Cys Gly Thr Pro Ala Glu Cys Val Leu Glu Gly Ala
            420                 425                 430

Glu Cys Cys Lys Lys Cys Thr Leu Thr Gln Asp Ser Gln Cys Ser Asp
            435                 440                 445

Gly Leu Cys Cys Lys Lys Cys Lys Phe Gln Pro Met Gly Thr Val Cys
    450                 455                 460

Arg Glu Ala Val Asn Asp Cys Asp Ile Arg Glu Thr Cys Ser Gly Asn
465                 470                 475                 480

Ser Ser Gln Cys Ala Pro Asn Ile His Lys Met Asp Gly Tyr Ser Cys
                485                 490                 495

Asp Gly Val Gln Gly Ile Cys Phe Gly Gly Arg Cys Lys Thr Arg Asp
                500                 505                 510

Arg Gln Cys Lys Tyr Ile Trp Gly Gln Lys Val Thr Ala Ser Asp Lys
            515                 520                 525

Tyr Cys Tyr Glu Lys Leu Asn Ile Glu Gly Thr Glu Lys Gly Asn Cys
    530                 535                 540

Gly Lys Asp Lys Asp Thr Trp Ile Gln Cys Asn Lys Arg Asp Val Leu
545                 550                 555                 560

Cys Gly Tyr Leu Leu Cys Thr Asn Ile Gly Asn Ile Pro Arg Leu Gly
                565                 570                 575

Glu Leu Asp Gly Glu Ile Thr Ser Thr Leu Val Val Gln Gln Gly Arg
                580                 585                 590

Thr Leu Asn Cys Ser Gly Gly His Val Lys Leu Glu Glu Asp Val Asp
            595                 600                 605

Leu Gly Tyr Val Glu Asp Gly Thr Pro Cys Gly Pro Gln Met Met Cys
    610                 615                 620

Leu Glu His Arg Cys Leu Pro Val Ala Ser Phe Asn Phe Ser Thr Cys
625                 630                 635                 640

Leu Ser Ser Lys Glu Gly Thr Ile Cys Ser Gly Asn Gly Val Cys Ser
                645                 650                 655

Asn Glu Leu Lys Cys Val Cys Asn Arg His Trp Ile Gly Ser Asp Cys
                660                 665                 670

Asn Thr Tyr Phe Pro His Asn Asp Asp Ala Lys Thr Gly Ile Thr Leu
            675                 680                 685

Ser Gly Asn Gly Val Ala Gly Thr Asn Ile Ile Gly Ile Ile Ala
    690                 695                 700

Gly Thr Ile Leu Val Leu Ala Leu Ile Leu Gly Ile Thr Ala Trp Gly
705                 710                 715                 720

Tyr Lys Asn Tyr Arg Glu Gln Arg Gln Leu Pro Gln Gly Asp Tyr Val
                725                 730                 735

Lys Lys Pro Gly Asp Gly Cys Ser Phe Tyr Ser Asp Ile Pro Pro Gly
            740                 745                 750

Val Ser Thr Asn Ser Ala Ser Ser Lys Lys Arg Ser Asn Gly Leu
    755                 760                 765

Ser His Ser Trp Ser Glu Arg Ile Pro Asp Thr Lys His Ile Ser Asp
            770                 775                 780

Ile Cys Glu Asn Gly Arg Pro Arg Ser Asn Ser Trp Gln Gly Asn Leu
785                 790                 795                 800
```

-continued

```
Gly Gly Asn Lys Lys Ile Arg Gly Lys Arg Phe Arg Pro Arg Ser
            805                 810                 815

Asn Ser Thr Glu Thr Leu Ser Pro Ala Lys Ser Pro Ser Ser Thr
        820                 825                 830

Gly Ser Ile Ala Ser Ser Arg Lys Tyr Pro Tyr Pro Met Pro Pro Leu
        835                 840                 845

Pro Asp Glu Asp Lys Lys Val Asn Arg Gln Ser Ala Arg Leu Trp Glu
    850                 855                 860

Thr Ser Ile
865

<210> SEQ ID NO 7
<211> LENGTH: 34
<212> TYPE: DNA
<213> ORGANISM: Homo sapiens

<400> SEQUENCE: 7
tatcttccta aaaagttcac ccagtgtaat attg                              34

<210> SEQ ID NO 8
<211> LENGTH: 27
<212> TYPE: DNA
<213> ORGANISM: Homo sapiens

<400> SEQUENCE: 8
tgctttctat tcccatcaga atagccc                                      27

<210> SEQ ID NO 9
<211> LENGTH: 23
<212> TYPE: DNA
<213> ORGANISM: Homo sapiens

<400> SEQUENCE: 9 cttttttacag agaggaggtg gag                                         23

<210> SEQ ID NO 10
<211> LENGTH: 23
<212> TYPE: DNA
<213> ORGANISM: Homo sapiens

<400> SEQUENCE: 10
gaaacaccag agactgagaa tgc                                          23
```

METALLOPROTEASE-DISINTEGRIN ADAM23 (SVPH3-17)

CROSS-REFERENCE TO RELATED APPLICATIONS

This application is a division of application U.S. Ser. No. 10/202,675, filed Jul. 23, 2002, now U.S. Pat. No. 7,196,168; which is a division of application U.S. Ser. No. 09/634,252, filed Aug. 7, 2000, now U.S. Pat. No. 6,787,644; which is a continuation of International Application number PCT/US99/03016, filed Feb. 11, 1999 and published in English on Aug. 19, 1999; which claims the benefit under 35 U.S.C. §119(e) of U.S. Provisional Application Ser. No. 60/074,310, filed Feb. 11, 1998; all of which are incorporated by reference herein.

BACKGROUND OF THE INVENTION

1. Field of the Invention

The invention is directed to purified and isolated novel members of the metalloproteinase-disintegrin family, specifically, SVPH3-13 and SVPH3-17 polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

Proteins Containing Disintegrin and Metalloproteinase Domains

Metalloproteinases are a group of proteinases characterized by the presence of a metal prosthetic group. Despite this basic similarity, the group, which includes proteinases from snake venom, numerous microbial proteinases, and vertebrate and bacterial collagenases, would seem to present proteinases of seemingly widely varying activities. For example, snake venom proteases are metalloproteinases that affect cell-matrix interactions. Snake venom also includes "disintegrins," a class of low molecular weight, Arg-Gly-Asp (RGD)-containing, cysteine-rich peptides which bind to integrins (a family of molecules involved in cell-to-cell adhesion, cell-to-matrix adhesion, and inflammatory responses) expressed on cells.

Also included are the membrane-anchored ADAMs (A Disintegrin And Metalloproteinase), which are multimeric molecules consisting of metalloproteinase, disintegrin-like, cysteine rich, and epidermal growth factor domains. See Black, R. A. and White, J. M., (1998) "ADAMS: focus on the protease domain," Curr Opin Cell Biol 10, 654-659 (in process); Wolfsberg, T. G. and White, J. M. (1996) "ADAMs in fertilization and development," Dev Bio 180, 389-401, all of which are herein incorporated by reference. The ADAMs family includes fertilin-α and meltrin-α, both of which are involved in membrane or cell-cell fusion. Specifically, the disintegrin domain of fertilin-α and meltrin-α have been implicated in sperm/egg fusion and myoblast fusion, respectively.

Another member of this family, ADAM 10/KUZ, has been identified as being involved in neurogenesis. (Id.)

The ADAMs family of metalloproteinase-disintegrins also share homology with the snake venom protease family (SVPH). In some snake venom protease members, the disintegrin domain prevents platelet aggregation and thus acts as an anti-coagulant. ADAMs and SVMPs share an extended catalytic site sequence and an activation mechanism, which involves proteolytic removal of the Pro domain. (Id.) In vitro cleavage of extracellular matrix molecules and cell surface proteins by ADAMs and SVMPs has been seen.

The ADAMs family members display a common domain organization, corresponding to potential proteolysis, adhesion, signaling, and fusion functions of these proteins. (Id.) Since several ADAMs have been shown to interact with integrins, bidirectional signaling is possible. (Id.) Some of the ADAMs are active proteinases.

Roles for ADAMs in matrix degradation, cell migration, and localized shedding of proteins including cytokines and growth factors have been reported. (Id.) For example, tumor necrosis factor a is cleaved by ADAM 17 to release a soluble form of the protein (Black et al., Nature 385:729-733, 1997; and Moss et al., Nature 385:733-736, 1997).

ADAMS 1-6 have been implicated in fertilization and/or spermatogenesis (Barker, H. L., Perry, A. C., Jones, R., and Hall, L., Biochim Biophys Acta, 1218, 429-31, 1994; Blobel, C. P., Wolfsberg, T. G., Turck, C. W., Myles, D. G., Primakoff, P., and White, J. M., Nature, 356, 248-252, 1992; Evans, J. P., Schultz, R. M., and Kopf, G. S., J. Cell Sci, 108, 3267-3278, 1995; Perry, A. C., Barker, H. L., Jones, R., and Hall., L., Biochim Biophsy Acta, 1207, 134-137, 1994; Perry, A. C., Gichuhi, P. M., Jones, R., and Hall, L., Biochem J., 307, 843-850, 1995; Perry, A. C., Jones, R., and Hall, L., Biochem J., 312, 239-244, 1995; Wolfsberg, T. G., Bazan, J. F., Blobel, C. P., Mules, D. G., Primakoff, P., and White, J. M., Proc Natl Acad Sci USA, 90, 10783-10787, 1993; and Wolfsberg, T. G., Straight, P. D., Gerena, R. L., Huovila, A. P., Primakoff, P., Myles, D. G., and White, J. M., Dev Biol, 169, 378-383, 1995).

The ADAMs family also includes the TNF-α converting enzymes (TACE). See Blobel, C. P, (1997), "The Metallo-disintegrins: Links to cell adhesion and cleavage of TNFa and notch," Cell 90, 589-592. TACE is required for the shedding of membrane proteins including TNF α, p80 TNFR, p60TNFR, L-selectin, type II IL-1R, and β-amyloid precursor protein.

Given the significant function of metalloproteinases in membrane and cell-cell fusion, cellular adhesion, shedding of membrane proteins, anti-coagulation, and neurogenesis there is a need in the art for additional metalloproteinases, of the ADAMs family and/or of the SVPH family members, including the discovery, identification, and roles of new proteins within these families.

Molecular Weight and Isoelectric Point Determinations

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, Biology of Microorganisms 76-77 (Prentice Hall, 6d ed. 1991)). Protein molecular weight standards are commercially available to assist in the estimation of molecular weights of unknown protein (New England Biolabs Inc. Catalog:130-131, 1995; J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., *J. Biol. Chem.* 252:1102-1106, 1977; M. Brown et al., *J. Gen. Virol.* 50:309-316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76-77 (Prentice Hall, 6d ed. 1991)).

Fragmentation of proteins is further employed for amino acid composition analysis and protein sequencing (P. Matsudiara, *J. Biol. Chem.* 262:10035-10038, 1987; C. Eckerskorn et al., *Electrophoresis* 1988, 9:830-838, 1988), particularly the production of fragments from proteins with a "blocked" N-terminus. In addition, fragmented proteins can be used for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300-301 (Prentice Hall, 6d ed. 1991)), and for differentiation of homologous proteins (M. Brown et al., *J. Gen. Virol.* 50:309-316, 1980).

In addition, when a peptide fingerprint of an unknown protein is obtained, it can be compared to a database of known proteins to assist in the identification of the unknown protein using mass spectrometry (W. J. Henzel et al., *Proc. Natl. Acad. Sci. USA* 90:5011-5015, 1993; D. Fenyo et al., *Electrophoresis* 19:998-1005, 1998). A variety of computer software programs to facilitate these comparisons are accessible via the Internet, such as Protein Prospector (prospector.uscf.edu), Multildent (expasy.ch/sprot/multiident), PeptideSearch (mann.embl-heiedelberg.de . . . deSearch/FR_PeptideSearch Form), and ProFound (chait-sgi.rockefeller.edu/cgi-bin/prot-id-frag). These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining the number of fragmented peptides and their molecular weight should result in enhanced likelihood of success in the identification of unknown proteins.

In addition, peptide digests of unknown proteins can be sequenced using tandem mass spectrometry (MS/MS) and the resulting sequence searched against databases (J. K. Eng, et al., *J. Am. Soc. Mass Spec.* 5:976-989 (1994); M. Mann and M. Wilm, *Anal. Chem.* 66:4390-4399 (1994); J. A. Taylor and R. S. Johnson, *Rapid Comm. Mass Spec.* 11:1067-1075 (1997)). Searching programs that can be used in this process exist on the Internet, such as Lutefisk 97 (lsbc.com:70/Lutefisk97), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there also exists a need in the art for polypeptides suitable for use in peptide fragmentation studies, for use in molecular weight measurements, and for use in protein sequencing using tandem mass spectrometry.

SUMMARY OF THE INVENTION

The invention aids in fulfilling these various needs in the art by providing new members of the metalloproteinase-disintegrin family, specifically, SVPH3-13 and SVPH3-17 nucleic acids and polypeptides encoded by these nucleic acids. Particular embodiments of the invention are directed to an isolated SVPH3-13 or SVPH3-17 nucleic acid molecule comprising the DNA sequence of SEQ ID NO:1, SEQ ID NO:2, or SEQ ID NO:5 and an isolated SVPH3-13 or SVPH3-17 nucleic acid molecule encoding the amino acid sequence of SEQ ID NO:3, SEQ ID NO:4, or SEQ ID NO:6, as well as nucleic acid molecules complementary to these sequences. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins having proteinase activity; to identify human chromosome number 2 or 7; to map genes on human chromosome number 2 or 7, to identify genes associated with certain diseases, syndromes, or other human conditions associated with human chromosome number 2 or 7.

The invention also encompasses the use of sense or antisense oligonucleotides from the nucleic acid of SEQ ID NO:1, SEQ ID NO:2, or SEQ ID NO:5 to inhibit the expression of the polynucleotide encoded by the SVPH3-13 or SVPH3-17 gene.

The invention also encompasses isolated polypeptides and fragments thereof encoded by these nucleic acid molecules including soluble polypeptide portions of SEQ ID NO:3, SEQ ID NO:4, or SEQ ID NO:6. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell death, cell migration, cell-to-cell interaction, and inflammatory responses.

In addition, the invention includes assays utilizing these polypeptides to screen for potential inhibitors of activity associated with polypeptide counter-structure molecules, and methods of using these polypeptides as therapeutic agents for the treatment of diseases mediated by SVPH polypeptide counter-structure molecules. Further, methods of using these polypeptides in the design of inhibitors thereof are also an aspect of the invention.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations. The invention further encompasses a kit for the determination of the molecular weights of peptide fragments of a sample protein comprising the following: a vessel; an SVPH3-13 or SVPH3-17 polypeptide; at least one enzyme selected from the group consisting of Asparaginylendopeptidase, Arginylendopeptidase, *Achrombobacter* protease I, Trypsin, *Staphlococcus aureus* V8 protease, Endoproteinase Asp-N, and Endoproteinase Lys-C; a mutated polypeptide derived from said polypeptide by in vitro mutagenesis, wherein a site of enzymatic cleavage by the selected enzyme has been removed; and fragmented peptides derived from said peptide by enzymatic cleavage with the selected enzyme; wherein said polypeptide and said sample protein are contacted with the selected protease; and wherein the protein, polypeptides, and fragmented peptides are visualized by application of the protein, polypeptides, and fragmented peptides to an acrylamide gel, resolution of the protein, polypeptides, and fragmented peptides using an electrical current, and application to the gel of a detection reagent, which stains the protein, polypeptides, and fragmented peptides.

Further encompassed by this invention is the use of the SVPH3-13 and SVPH3-17 nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition the use of these antibodies to aid in purifying SVPH3-13 and SVPH3-17 polypeptides.

Figure 1:
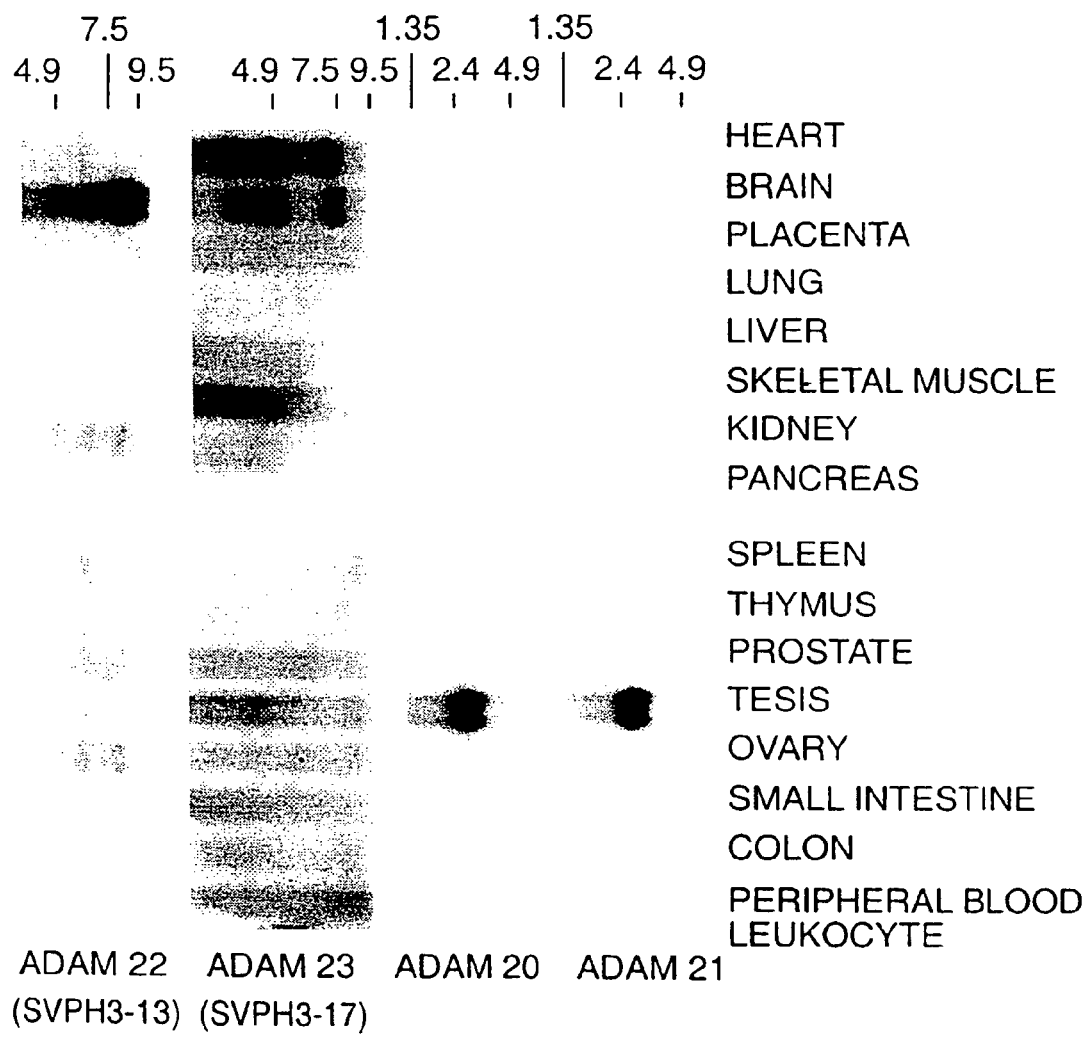
FIG. 1 presents expression data of SVPH3-13 and SVPH3-17 RNA in various tissues by Northern blot.

DETAILED DESCRIPTION OF THE INVENTION cDNAs encoding human SVPH3-13 and 3-17 polypeptides have been isolated and are disclosed in SEQ ID NO:1 and SEQ ID NO:2:

```
                                                   (SEQ ID NO:1)
CTTCTTGATCCTCCTGAGTGTGGCAATGGCTTCATTGAAACTGGAGAGGA

GTGTGATT
                                                   (SEQ ID NO:2)
ATGAAGCCGCCCGGCAGCAGCTCGCGGCAGCCGCCCCTGGCGGGCTGCAG

CCTTGCCGGCGCTTCCTGCGGCCCCCAACGCGGCCCCGCCGGCTCGGTGC

CTGCCAGCGCCCCGGCCCGCACGCCGCCCTGCCGCCTGCTTCTCGTCCTT

CTCCTGCTGCCTCCGCTCGCCGCCTCGTCCCGGCCCCGCGCCTGGGGGGC

TGCTGCGCCCAGCGCTCCGCATTGGAATGAAACTGCAGAAAAAAATTTGG

GAGTCCTGGCAGATGAAGACAATACATTGCAACAGAATAGCAGCAGTAAT

ATCAGTTACAGCAATGCAATGCAGAAAGAAATCACACTGCCTTCAAGACT
```

```
                                                   -continued
CATATATTACATCAACCAAGACTCGGAAAGCCCTTATCACGTTCTTGACA

CAAAGGCAAGACACCAGCAAAAACATAATAAGGCTGTCCATCTGGCCCAG

GCAAGCTTCCAGATTGAAGCCTTCGGCTCCAAATTCATTCTTGACCTCAT

ACTGAACAATGGTTTGTTGTCTTCTGATTATGTGGAGATTCACTACGAAA

ATGGGAAACCACAGTACTCTAAGGGTGGAGAGCACTGTTACTACCATGGA

AGCATCAGAGGCGTCAAAGACTCCAAGGTGGCTCTGTCAACCTGCAATGG

ACTTCATGGCATGTTTGAAGATGATACCTTCGTGTATATGATAGAGCCAC

TAGAGCTGGTTCATGATGAGAAAAGCACAGGTCGACCACATATAATCCAG

AAAACCTTGGCAGGACAGTATTCTAAGCAAATGAAGAATCTCACTATGGA

AAGAGGTGACCAGTGGCCCTTTCTCTCTGAATTACAGTGGTTGAAAAGAA

GGAAGAGAGCAGTGAATCCATCACGTGGTATATTTGAAGAAATGAAATAT

TTGGAACTTATGATTGTTAATGATCACAAAACGTATAAGAAGCATCGCTC

TTCTCATGCACATACCAACAACTTTGCAAAGTCCGTGGTCAACCTTGTGG

ATTCTATTTACAAGGAGCAGCTCAACACCAGGGTTGTCCTGGTGGCTGTA

GAGACCTGGACTGAGAAGGATCAGATTGACATCACCACCAACCCTGTGCA

GATGCTCCATGAGTTCTCAAAATACCGGCAGCGCATTAAGCAGCATGCTG

ATGCTGTGCACCTCATCTCGCGGGTGACATTTCACTATAAGAGAAGCAGT

CTGAGTTACTTTGGAGGTGTCTGTTCTCGCACAAGAGGAGTTGGTGTGAA

TGAGTATGGTCTTCCAATGGCAGTGGCACAAGTATTATCGCAGAGCCTGG

CTCAAAACCTTGGAATCCAATGGGAACCTTCTAGCAGAAAGCCAAAATGT

GACTGCACAGAATCCTGGGGTGGCTGCATCATGGAGGAAACAGGGGTGTC

CCATTCTCGAAAATTTTCAAAGTGCAGCATTTTGGAGTATAGAGACTTTT

TACAGAGAGGAGGTGGAGCCTGCCTTTTCAACAGGCCAACAAAGCTATTT

GAGCCCACGGAATGTGGAAATGGATACGTGGAAGCTGGGGAGGAGTGTGA

TTGTGGTTTTCATGTGGAATGCTATGGATTATGCTGTAAGAAATGTTCCC

TCTCCAACGGGGCTCACTGCAGCGACGGGCCCTGCTGTAACAATACCTCA

TGTCTTTTTCAGCCACGAGGGTATGAATGCCGGGATGCTGTGAACGAGTG

TGATATTACTGAATATTGTACTGGAGACTCTGGTCAGTGCCCACCAAATC

TTCATAAGCAAGACGGATATGCATGCAATCAAAATCAGGGCCGCTGCTAC

AATGGCGAGTGCAAGACCAGAGACAACCAGTGTCAGTACATCTGGGGAAC

AAAGGCTGCAGGGTCTGACAAGTTCTGCTATGAAAAGCTGAATACAGAAG

GCACTGAGAAGGGAAACTGCGGGAAGGATGGAGACCGGTGGATTCAGTGC

AGCAAACATGATGTGTTCTGTGGATTCTTACTCTGTACCAATCTTACTCG

AGCTCCACGTATTGGTCAACTTCAGGGTGAGATCATTCCAACTTCCTTCT

ACCATCAAGGCCGGTGATTGACTGCAGTGGTGCCCATGTAGTTTTAGAT

GATGATACGGATGTGGGCTATGTAGAAGATGGAACGCCATGTGGCCCGTC

TATGATGTGTTTAGATCGGAAGTGCCTACAAATTCAAGCCCTAAATATGA

GCAGCTGTCCACTCGATTCCAAGGGTAAAGTCTGFCCGGGCCATGGGGTG

TGTAGTAATGAAGCCACCTGCATTTGTGATTTCACCTGGGCAGGGACAGA

TTGCAGTATCCGGGATCCAGTTAGGAACCTTCACCCCCCCAAGGATGAAG
```

-continued

```
GACCCAAGGGTCCTAGTGCCACCAATCTCATAATAGGCTCCATCGCTGGT

GCCATCCTGGTAGCAGCTATTGTCCTTGGGGGCACAGGCTGGGGATTTAA

AAATGTCAAGAAGAGAAGGTTCGATCCTACTCAGCAAGGCCCCATCTGA
```

SEQ ID NO:1 and SEQ ID NO:2 encode SVPH3-13 and SVPH3-17 polypeptides disclosed in SEQ ID NO:3 and SEQ ID NO:4:

```
                                              (SEQ ID NO:3)
LLDPPECGNGFIETGEECDC (SEQ ID NO:4)
MKPPGSSSRQPPLAGCSLAGASCGPQRGPAGSVPASAPARTPPCRLLLVL

LLLPPLAASSRPRAWGAAAPSAPHWNETAEKNLGVLADEDNTLQQNSSSN

ISYSNAMQKEITLPSRLIYYINQDSESPYHVLDTKARHQQKHNKAVHLAQ

ASFQIEAFGSKFILDLILNNGLLSSDYVEIHYENGKPQYSKGGEHCYYHG

SIRGVKDSKVALSTCNGLHGMFEDDTFVYMIEPLELVHDEKSTGRPHIIQ

KTLAGQYSKQMKNLTMERGDQWPFLSELQWLKRRKRAVNPSRGIFEEMKY

LELMIVNDHKTYKKHRSSHAHTNNFAKSVVNLVDSIYKEQLNTRVVLVAV

ETWTEKDQIDITTNPVQMLHEFSKYRQRIKQHADAVHLISRVTFHYKRSS

LSYFGGVCSRTRGVGVNEYGLPMAVAQVLSQSLAQNLGIQWEPSSRKPKC

DCTESWGGCIMEETGVSHSRKFSKCSILEYRDFLQRGGGACLFNRPTKLF

EPTECGNGYVEAGEECDCGFHVECYGLCCKKCSLSNGAHCSDGPCCNNTS

CLFQPRGYECRDAVNECDITEYCTGDSGQCPPNLHKQDGYACNQNQGRCY

NGECKTRDNQCQYIWGTKAAGSDKYCYEKLNTEGTEKGNCGKDGDRWIQC

SKHDVFCGFLLCTNLTRAPRIGQLQGEIIPTSFYHQGRVIDCSGAHVVLD

DDTDVGYVEDGTPCGPSMMCLDRKCLQIQALNMSSCPLDSKGKVCSGHGV

CSNEATCICDFTWAGTDCSIRDPVRNLHPPKDEGPKGPSATNLIIGSIAG

AILVAAIVLGGTGWGFKNVKKRRFDPTQQGPI
```

A cDNA encoding a near full-length human SVPH3-13 polypeptide has been isolated and is disclosed in SEQ ID NO:5:

```
                                              (SEQ ID NO:5)
AAGGAAAACCGCTTCGTGGAGCGCCAGAGCATCGTGCCACTGCGCCTCAT

CTACCGCTCGGGCGGCAAGACGAAAGTCGGCACGACGCGCTCGACACGC

GGGTGCGGGGCGACCTCGGTGCCGGCAGTTGACTCATGTTGACCAAGCA

AGCTTCCAGGTTGATGCCTTTGGAACGTCATTCATTCTCGATGTCGTGCT

AAATCATGATTTGCTGTCCTCTGAATACATAGAGAGACACATTGAACATG

GAGGCAAGACTGTGGAAGTTAAAGGAGGAGAGCACTGTTACTACCAGGGC

CATATCCGAGGAAACCCTGACTCATTTGTTGCATTGTCAACATGCCACGG

ACTTCATGGGATGTTCTATGACGGGAACCACACATATCTCATTGAGCCAG

AAGAAAATGACACTACTCAAGAGGATTTCCATTTTCATTCAGTTTACAAA

TCCAGACTGTTTGAATTTTCCTTGGATGATCTTCCATCTGAATTTCAGCA

AGTAAACATTACTCCATCAAAATTTATTTTGAAGCCAAGACCAAAAGGA

GTAAACGGCAGCTTCGTCGATATCCTCGTAATGTAGAAGAAGAAACCAAA

TACATTGAACTGATGATTGTGAATGATCACCTTATGTTTAAAAAACATCG

GCTTTCCGTTGTACATACCAATACCTATGCGAAATCTGTGGTGAACATGG

CAGATTTAATATATAAAGACCAACTTAAGACCAGGATAGTATTGGTTGCT

ATGGAAACCTGGGCGACTGACAACAAGTTTGCCATATCTGAAAATCCATT

GATCACCCTACGTGAGTTTATGAAATACAGGAGGGATTTTATCAAAGAGA

AAAGTGATGCAGTTCACCTTTTTTCGGGAAGTCAATTTGAGAGTAGCCGG

AGCGGGGCAGCTTATATTGGTGGGATTTGCTCGTTGCTGAAAGGAGGAGG

CGTGAATGAATTTGGGAAAACTGATTTAATGGCTGTTACACTTGCCCAGT

CATTAGCCCATAATATTGGTATTATCTCAGACAAAAGAAAGTTAGCAAGT

GGTGAATGTAAATGCGAGGACACGTGGTCCGGGTGCATAATGGGAGACAC

TGGCTATTATCTTCCTAAAAAGTTCACCCAGTGTAATATTGAAGAGTATC

ATGACTTCCTGAATAGTGGAGGTGGTGCCTGCCTTTTCAACAAACCTTCT

AAGCTTCTTGATCCTCCTGAGTGTGGCAATGGCTTCATTGAAACTGGAGA

GGAGTGTGATTGTGGAACCCCGGCCGAATGTGTCCTTGAAGGAGCAGAGT

GTTGTAAGAAATGCACCTTGACTCAAGACTCTCAATGCAGTGACGGTCTT

TGCTGTAAAAAGTGCAAGTTTCAGCCTATGGGCACTGTGTGCCGAGAAGC

AGTAAATGATTGTGATATTCGTGAAACGTGCTCAGGAAATTCAAGCCAGT

GTGCCCCTAATATTCATAAAATGGATGGATATTCATGTGATGGTGTTCAG

GGAATTTGCTTTGGAGGAAGATGCAAAACCAGAGATAGACAATGCAAATA

CATTTGGGGGCAAAAGGTGACAGCATCAGACAAATATTGCTATGAGAAAC

TGAATATTGAAGGGACGGAGAAGGGTAACTGTGGGAAAGACAAAGACACA

TGGATACAGTGCAACAAACGGGATGTGCTTTGTGGTTACCTTTTGTGTAC

CAATATTGGCAATATCCCAAGGCTTGGAGAACTCGATGGTGAAATCACAT

CTACTTTAGTTGTGCAGCAAGGAAGAACATTAAACTGCAGTGGTGGGCAT

GTTAAGCTTGAAGAAGATGTAGATCTTGGCTATGTGGAAGATGGGACACC

TTGTGGTCCCCAAATGATGTGCTTAGAACACAGGTGTCTTCCTGTGGCTT

CTTTCAACTTTAGTACTTGCTTGAGCAGTAAAGAAGGCACTATTTGCTCA

GGAAATGGAGTTTGCAGTAATGAGCTGAAGTGTGTGTGTAACAGACACTG

GATAGGTTCTGATTGCAACACTTACTTCCCTCACAATGATGATGCAAAGA

CTGGTATCACTCTGTCTGGCAATGGTGTTGCTGGCACCAATATCATAATA

GGCATAATTGCTGGCACCATTTTAGTGCTGGCCCTCATATTAGGAATAAC

TGCCGTGGGTTATAAAAACTATCGAGAACAGAGACAGTTACCCCAGGGAG

ATTATGTAAAAAAGCCTGGAGATGGTGACTCTTTTTATAGCGACATTCCT

CCCGGAGTCAGCACAAACTCAGCATCTAGTTCTAAGAAGAGGTCAAATGG

GCTCTCTCATTCTTGGAGTGAAAGGATTCCAGACACAAAACATATTTCAG

ACATCTGTGAAAATGGGCGACCTCGAAGTAACTCTTGGCAAGGTAACCTG

GGAGGCAACAAAAAGAAAATCAGAGGCAAAAGATTTAGACCTCGGTCTAA

TTCAACTGAGACTTTATCTCCTGCCAAGTCTCCTTCTTCATCAACTGGGT
```

-continued
```
CTATTGCCTCCAGCAGAAAATACCCTTACCCAATGCCTCCACTTCCTGAT

GAGGACAAGAAAGTGAACCGACAAAGTGCCAGGCTATGGGAGACATCCAT

TTAA
```

SEQ ID NO:5 encodes an SVPH3-13 polypeptide disclosed in SEQ ID NO:6:

```
                                              (SEQ ID NO:6)
KENFRVERQSIVPLRLIYRSGGEDESRHDALDTRVRGDLGGRQLTHVDQA

SFQVDAFGTSFILDVVLNGDLLSSEYIERHIEHGGKTVEVKGGEHCYYQG

HIRGNPDSFVALSTCHGLHGMFYDGNHTYLIEPEENDTTQEDFHFHSVYK

SRLFEFSLDDLPSEFQQVNITPSKFILKPRPKRSKRQLRRYPRNVEEETK

YIELMIVNDHLMFKKHRLSVVHTNTYAKSVVNMADLIYKDQLKTRIVLVA

METWATDNKFAISENPLITLREFMAKYRRDHKEKSDAVHLFSGSQFESSR

SGAAYIGGICSLLKGGGVNEFGKTDLMAVTLAQSLAHNIGIISDKRKLAS

GECKCEDTWSGCLMGDTGYYLPKKFTQCNIEEYHDFLNSGGGACLFNKPS

KLLDPPECGNGFIETGEECDCGTPAECVLEGAECCKKCTLTQDSQCSDGL

CCKKCKFQPMGTVCREAVNDCDIRETCSGNSSQCAPNIHKMDGYSCDGVQ

GICFGGRCKTRDRQCKYIWGQKVTASDKYCYEKLNIEGTEKGNCGKDKDT

WIQCNKRDVLCGYLLCTNIGNIPRLGELDGEITSTLVVQQGRTLNCSGGH

VKLEEDVDLGYVEDGTPCGPQMMCLEHRCLPVASFNFSTCLSSKEGTICS

GNGVCSNELKCVCNRHWIGSDCNTYFPHNDDAKTGITLSGNGVAGTNIII

GIIAGTILVLALILGITAWGYKNYREQRQLPQGDYVKKPGDGCSFYSDIP

PGVSTNSASSSKKRSNGLSHSWSERIPDTKHISDICENGRPRSNSWQGNL

GGNKKKIRGKRFRPRSNSTETLSPAKSPSSSTGSIASSRKYPYPMYPLPD

EDKKVNRQSARLWETSI
```

This discovery of the cDNAs encoding human SVPH3-13 and 3-17 polypeptides enables construction of expression vectors comprising nucleic acid sequences encoding SVPH3-13 or 3-17 polypeptides; host cells transfected or transformed with the expression vectors; biologically active human SVPH3-13 and 3-17 proteinase and SVPH3-13 and 3-17 molecular weight markers as isolated and purified proteins; and antibodies immunoreactive with SVPH3-13 and 3-17 polypeptides.

SVPH3-13 and 3-17 proteinases are members of the snake venom protease family. SVPH3-13 (ADAM22) polypeptide (SEQ ID NO:3) encodes a portion of the disintegrin domain. SVPH3-13 (ADAM22) DNA (SEQ ID NO:5) encodes an SVPH3-13 (ADAM22) polypeptide (SEQ ID NO:6), which lacks a portion of the amino terminal signal sequence.

SVPH3-17 polypeptide (SEQ ID NO:4) has all of the conserved domain structures found in mammalian ADAMs: signal sequence (amino acids 1-58 of SEQ ID NO:4), pro domain (amino acids 59-286 of SEQ ID NO:4), "catalytic" domain (amino acids 287-495 of SEQ ID NO:4), disintegrin domain (amino acids 496-599 of SEQ ID NO:4), Cys-rich domain (amino acids 600-786 of SEQ ID NO:4), transmembrane domain (amino acids 787-817 of SEQ ID NO:4), and a cytoplasmic domain (amino acids 818-832 of SEQ ID NO:4).

SVPH3-13 polypeptide (SEQ ID NO:6) does include an extracellular domain (amino acids 1-697 of SEQ ID NO:6), a transmembrane domain (amino acids 698-721 of SEQ ID NO:6), and an intracellular domain (amino acids 722-867 of SEQ ID NO:6). SVPH3-13 polypeptide (SEQ ID NO:6) also has the following domain structures found in mammalian adamalysins (ADAMS): disintegrin domain (amino acids 400-499 of SEQ ID NO:6) and a Cys-rich domain (amino acids 500-697 of SEQ ID NO:6).

SVPH3-13 and SVPH3-17 are missing the Zn binding motif found in some ADAMs.

SVPH3-13 (ADAM22) is specifically expressed in brain by Northern analysis (Example 1). SVPH3-17 (ADAM23) is specifically expressed in brain and heart by Northern analysis (Example 1). Therefore, SVPH3-13 and SVPH3-17 may be involved in neurogenesis.

SVPH3-13 DNA maps to the human chromosome locus 7q21. SVPH3-17 maps to the human chromosome locus 2q33.

SVPH3-13 and 3-17 polypeptides are homologous to the TACE protein. TACE is a proteinase required for the shedding of membrane proteins including TNF $\alpha$, p80 TNFR, p60TNFR, L-selectin, type II IL-1R, and $\beta$-amyloid precursor protein. SVPH3-13 and 3-17 proteinases also show homology with fertilin-$\alpha$, which is required for binding of sperm to egg; meltrin-$\alpha$, which is required for the fusion of myoblasts into muscle cells; reprolysin, which cleaves myelin basic protein; and kuzbanian, which is a *Drosophila* homologue of reprolysin which is required for neurogenesis and axonal extension. Thus, SVPH3-13 and 3-17 may be involved in the shedding of membrane proteins.

Additional preferred nucleotide sequences of the invention include isolated fragments and oligonucleotides derived from the nucleotide sequence of SEQ ID NO:1, SEQ ID NO:2, or SEQ ID NO:5. Particularly preferred sequences include nucleotides encoding the amino acid sequences 1-58, 59-286, 287-495, 496-599, 600-786, 787-817, and 818-832 of SEQ ID NO:4 and nucleotides encoding the amino acid sequences 1-697, 698-721, 722-867, 400-499, and 500-697 of SEQ ID NO:6. The invention also encompasses polypeptides encoded by these fragments and oligonucleotides.

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having SVPH activity. The invention also enables the use of the nucleic acids or oligonucleotides thereof to identify human chromosome number 2 or 7, to map genes on human chromosome number 2 or 7, and to identify genes associated with certain diseases, syndromes or other human conditions associated with human chromosome number 2 or 7. Diseases that correspond to chromosome number 7 include malignant hyperthermia susceptibility, Zellweger syndrome, noenatal adrenoleukodystrophy, infantile Refsum disease, progressive familial intrahepatic colchestatis, mucopolysaccharidosis VII, split hand/foot malformation, while those that correspond to chromosome number 2 include arrhythymogenic right ventricular displasia-4, insulin-dependent diabetes mellitus-12, transient neonatal myasthenia gravis, juvenile amyotropic lateral sclerosis, congenital aculeiform cataract, Coppock-like cataract, lamellar type ichthyosis, familial paroxysmal choreoathetosis, and Finnish lethal neonatal metabolic syndrome. The invention also provides the use of single-stranded sense or antisense oligonucleotides from the nucleic acids to inhibit expression of polynucleotide encoded by the SVPH3-13 or SVPH3-17 gene. Finally, the invention enables the use of such polypeptides and fragmented peptides as molecular weight markers; the use of such polypeptides and fragmented peptides as controls for peptide fragmentation, and kits comprising these reagents; as well as the use of such polypeptides and fragments thereof to generate antibodies and the use of antibodies to purify SVPH3-13 or SVPH3-17 polypeptides.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, SEQ ID NO:2, SEQ ID NO:5, or a suitable fragment thereof, as a probe.

The DNA molecules of the invention include full length genes as well as polynucleotides and fragments thereof. The full length gene may include the N-terminal signal peptide. Other embodiments include DNA encoding a soluble form, e.g., encoding the extracellular domain of the protein, either with or without the signal peptide.

The nucleic acids of the invention are preferentially derived from human sources, but the invention includes those derived from non-human species, as well.

Preferred Sequences

Particularly preferred nucleotide sequences of the invention are SEQ ID NO:1, SEQ ID NO:2, and SEQ ID NO:5, as set forth above.

Additional Sequences

Due to the known degeneracy of the genetic code, wherein more than one codon can encode the same amino acid, a DNA sequence can vary from that shown in SEQ ID NO:1, SEQ ID NO:2, and SEQ ID NO:5, and still encode a polypeptide having the amino acid sequence of SEQ ID NO:3, SEQ ID NO:4, or SEQ ID NO:6. Such variant DNA sequences can result from silent mutations (e.g., occurring during PCR amplification), or can be the product of deliberate mutagenesis of a native sequence.

The invention thus provides isolated SVPH DNA sequences encoding polypeptides of the invention, selected from: (a) DNA comprising the nucleotide sequence of SEQ ID NO:1, SEQ ID NO:2, or SEQ ID NO:5; (b) DNA encoding the polypeptides of SEQ ID NO:3, SEQ ID NO:4, and SEQ ID NO:6; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual,* 2 ed. Vol. 1, pp. 1.101-104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2× SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a SVPH3-13 or SVPH3-17 polypeptide, or desired fragment thereof, may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence SEQ ID NO:3, SEQ ID NO:4, and SEQ ID NO:6 with particularly preferred fragments comprising amino acids 1-58, 59-286, 287-495, 496-599, 600-786, 787-817, or 818-831 of SEQ ID NO:4, and amino acids 1-697, 698-721, 722-867, 400-499, or 500-697 of SEQ ID NO:6.

As used herein, the term "SVPH3-13 and 3-17 polypeptides" refers to a genus of polypeptides that further encompasses proteins having the amino acid sequence 1-20 of SEQ ID NO:3 or 1-867 of SEQ ID NO:6 and 1-832 of SEQ ID NO:4, respectively, as well as those proteins having a high degree of similarity (at least 90% homology) with such amino acid sequences and which proteins are biologically active. In addition, SVPH3-13 and 3-17 polypeptides refers to the gene products of the nucleotides 1-58 of SEQ ID NO:1 or 1-2601 of SEQ ID NO:5 and nucleotides 1-2499 of SEQ ID NO:2, respectively.

The isolated and purified SVPH3-13 (SEQ ID NO:3 and SEQ ID NO:6) and SVPH3-17 (SEQ ID NO:4) polypeptides according to the invention have molecular weights of approximately 2,139 or 96,450 and 91,866 Daltons in the absence of glycosylation, respectively. It is understood that the molecular weight of SVPH3-13 and 3-17 polypeptides can be varied by fusing additional peptide sequences to both the amino and carboxyl terminal ends of SVPH3-13 and 3-17 polypeptides. Fusions of additional peptide sequences at the amino and carboxyl terminal ends of SVPH3-13 and 3-17 polypeptides can be used to enhance expression of SVPH3-13 and 3-17 polypeptides or aid in the purification of the protein.

The skilled artisan will recognize that the above-described boundaries of such regions of the polypeptide are approximate and that the boundaries of the transmembrane region (which may be predicted by using computer programs available for that purpose) may differ from those described above.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

Additional examples of soluble polypeptides are those lacking not only the cytoplasmic domain and transmembrane region, but also all or part of the above-described spacer region.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Particular embodiments are directed to polypeptide fragments that retain the ability to bind the native substrates. Such a fragment may be a soluble polypeptide, as described above. In another embodiment, the polypeptides and fragments advantageously include regions that are conserved in the ADAM family as described above.

Also provided herein are polypeptide fragments comprising at least 20, or at least 30, contiguous amino acids of the sequence of SEQ ID NO:3, SEQ ID NO:4, or SEQ ID NO:6. Fragments derived from the cytoplasmic domain find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

An SVPH3-13 or 3-17 polypeptide "variant" as referred to herein means a polypeptide substantially homologous to native SVPH3-13 or 3-17 polypeptides, but which has an amino acid sequence different from that of native SVPH3-13 and 3-17 polypeptides (human, murine or other mammalian species) because of one or more deletions, insertions or substitutions. The variant amino acid sequence preferably is at least 80% identical to a native SVPH3-13 or 3-17 polypeptide amino acid sequence, most preferably at least 90% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof.

The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 351-2658, 1979; (2) a penalty of 3.0 for each gap and an additional 0.10 penalty for each symbol in each gap; and (3) no penalty for end gaps.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

As stated above, the invention provides isolated and purified, or homogeneous, SVPH3-13 and 3-17 polypeptides, both recombinant and non-recombinant. Variants and derivatives of native SVPH3-13 and 3-17 polypeptides that can be used as molecular weight markers can be obtained by mutations of nucleotide sequences coding for native SVPH3-13 and 3-17 polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene, wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212, 914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain SVPH3-13 or SVPH3-17 polypeptides. Such oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four SVPH3-13 or SVPH3-17 extracellular regions.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble SVPH3-13 or SVPH3-17 polypeptides, separated by peptide linkers.

Leucine-zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form heterodimer (O'Shea et al., *Science* 245:646, 1989, Turner and Tjian, *Science* 243: 1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated (abc-defg)$_n$, according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al (*Science* 262:1401, 26 Nov. 1993).

Examples of leucine zipper domains suitable for producing soluble oligomeric proteins are described in PCT application WO 94/10308, as well as the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD) noted above, as described in Hoppe et al. (*FEBS Letters* 344:191, 1994) and in U.S. Pat. No. 5,716, 805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr.

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg, as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric SVPH3-13 or SVPH3-17 polypeptides. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site. Particular embodiments of mature proteins provided herein include, but are not limited to, proteins having the residue at position 59 or 287 of SEQ ID NO:4 as the N-terminal amino acid.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

For expression of the recombinant protein, the bacterial cells are propagated in growth medium until reaching a predetermined optical density. Expression of the recombinant protein is then induced, e.g. by addition of IPTG (isopropyl-b-D-thiogalactopyranoside), which activates expression of proteins from plasmids containing a lac operator/promoter. After induction (typically for 1-4 hours), the cells are harvested by pelleting in a centrifuge, e.g. at 5,000×G for 20 minutes at 4° C.

For recovery of the expressed protein, the pelleted cells may be resuspended in ten volumes of 50 mM Tris-HCl (pH 8)/1 M NaCl and then passed two or three times through a French press. Most highly-expressed recombinant proteins form insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTT. Any material that cannot be dissolved is removed by centrifugation (10,000×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be carried out by a variety of chromatographic methods, such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind SVPH counterstructures in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing SVPH counterstructures. The cells then are washed to remove unbound labeled polypeptide, and the presence of cell-bound label is determined by a suitable technique, chosen according to the nature of the label.

In addition, the cleavage of an SVPH counterstructure by SVPH3-13 or SVPH3-17 can be assessed by conventional assays of proteolysis.

One example of a binding assay procedure is as follows. A recombinant expression vector containing an SVPH counterstructure is constructed. The SVPH counterstructure comprises an N-terminal cytoplasmic domain, a transmembrane region, and a C-terminal extracellular domain. CV1-EBNA-1 cells in 10 $cm^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about $4\times10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a variant may be determined by assaying for the variant's ability to compete with the native protein for binding to SVPH counterstructures.

Competitive binding assays can be performed by conventional methodology. Reagents that may be employed in competitive binding assays include radiolabeled SVPH3-13 or SVPH3-17 and intact cells expressing SVPH counterstructures (endogenous or recombinant) on the cell surface. For example, a radiolabeled soluble SVPH fragment can be used to compete with a soluble SVPH variant for binding to cell surface SVPH counterstructures. Instead of intact cells, one could substitute a soluble SVPH counterstructure/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble SVPH counterstructure, such as a soluble SVPH counterstructure/Fc fusion protein, and intact cells expressing an SVPH3-13 or SVPH3-17 polypeptide. Qualitative results can be obtained by competitive autoradiographic plate binding assays, while Scatchard plots (Scatchard, *Ann. N.Y. Acad. Sci.* 51:660, 1949) may be utilized to generate quantitative results.

Use of SVPH3-13 or SVPH3-17 Nucleic Acid or Oligonucleotides

In addition to being used to express polypeptides as described above, the nucleic acids of the invention, including DNA, and oligonucleotides thereof can be used:

- as probes to identify nucleic acid encoding proteins having metalloproteinase-disintegrin activity;
- to identify human chromosome number 2 or 7;
- to map genes on human chromosome number 2 or 7;
- to identify genes associated with certain diseases, syndromes, or other conditions associated with human chromosome number 2 or 7; and
- as single-stranded sense or antisense oligonucleotides, to inhibit expression of polypeptide encoded by the SVPH3-13 or SVPH3-17 gene.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1, SEQ ID NO:2, and SEQ ID NO:5 from other mammalian species are contemplated herein, probes based on the human DNA sequence of SEQ ID NO:1, SEQ ID NO:2, and SEQ ID NO:5 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

All or a portion of the nucleic acids of SEQ ID NO:1 and SEQ ID NO:5, including oligonucleotides, can be used by those skilled in the art using well-known techniques to identify the human chromosome 7, and the specific locus 7q21, that contains the DNA of SVPH3-13 family members.

Similarly, all or a portion of the nucleic acids of SEQ ID NO:2, including oligonucleotides, can be used by those skilled in the art using well-known techniques to identify the human chromosome 2, and the specific locus 2q33, that contains the DNA of SVPH3-17 (ADAM23) family members.

Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. First, PCR is performed using the Whitehead Institute/MIT Center for Genome Research Genebridge4 panel of 93 radiation hybrids (genome.wi.mit.edu/ftp/distribution/human_STS_releases/july97/rhmap/genebridge4). Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (seq.wi.mit.edu). The data is scored and the chromosomal assignment and placement relative to known Sequence Tag Site (STS) markers on the radiation hybrid map is provided. The following web site provides additional information about radiation hybrid mapping: genome.wi.mit.edu/ftp/distribution/human_STS_releases/july97/07-97.INTRO).

Identifying Associated Diseases

SVPH3-13 (SEQ ID NO:1 and SEQ ID NO:5) has been mapped by radiation-hybrid mapping to human chromosome region 7q21 (Example 2). That region is associated with specific diseases which include but are not limited to malignant hyperthermia susceptibility, Zellweger syndrome, noenatal adrenoleukodystrophy, infantile Refsum disease, progressive familial intrahepatic colchestatis, mucopolysaccharidosis VII, and split hand/foot malformation. Thus, the nucleic acid of SEQ ID NO:1 and SEQ ID NO:5 or a fragment thereof can be used by one skilled in the art using well-known techniques to analyze abnormalities associated with gene mapping to chromosome 7. This enables one to distinguish conditions in which this marker is rearranged or deleted. In addition, nucleotides of SEQ ID NO:1 and SEQ ID NO:5 or a fragment thereof can be used as a positional marker to map other genes of unknown location.

SVPH3-17 (SEQ ID NO:2) has been mapped by radiation-hybrid mapping to human chromosome region 2q33 (Example 2). That region is associated with specific diseases which include but are not limited to arrhythymogenic right ventricular displasia-4, insulin-dependent diabetes mellitus-12, transient neonatal myasthenia gravis, juvenile amyotropic lateral sclerosis, congenital aculeiform cataract, Coppock-like cataract, lamellar type ichthyosis, familial paroxysmal choreoathetosis, and Finnish lethal neonatal metabolic syndrome. Thus, the nucleic acid of SEQ ID NO:2 or a fragment thereof can be used by one skilled in the art using well-known techniques to analyze abnormalities associated with gene mapping to chromosome 2. This enables one to distinguish conditions in which this marker is rearranged or deleted. In addition, nucleotides of SEQ ID NO:2 or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of SVPH3-13 or SVPH3-17 DNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Use of SVPH3-13 and 3-17 Polypeptides and Fragmented Polypeptides

Uses include, but are not limited to, the following:
Purifying proteins and measuring activity thereof
Delivery Agents
Detergent Additives
Therapeutic and Research Reagents
Molecular weight and Isoelectric focusing markers
Controls for peptide fragmentation Identification of unknown proteins
Preparation of Antibodies
Purification Reagents The polypeptides of the invention find use as protein purification reagents. The polypeptides may be used to purify SVPH counterstructure proteins by affinity chromatography. In particular embodiments, a polypeptide (in any form described herein that is capable of binding SVPH counterstructure) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express an SVPH counterstructure on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing SVPH counterstructure expressing cells are contacted with the solid phase having the polypeptides thereon. Cells expressing SVPH counterstructure on the cell surface bind to the fixed polypeptides, and unbound cells then are washed away.

Alternatively, the polypeptides can be conjugated to a detectable moiety, then incubated with cells to be tested for SVPH counterstructure expression. After incubation, unbound labeled matter is removed and the presence or absence of the detectable moiety on the cells is determined.

In a further alternative, mixtures of cells suspected of containing SVPH counterstructure cells are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Measuring Activity

Polypeptides also find use in measuring the biological activity of SVPH counterstructure protein in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a SVPH counterstructure protein that has been stored at different temperatures, or produced in different cell types. The proteins also may be used to determine whether biological activity is retained after modification of a SVPH counterstructure protein (e.g., chemical modification, truncation, mutation, etc.). The binding affinity of the modified SVPH counterstructure protein is compared to that of an unmodified SVPH counterstructure protein to detect any adverse impact of the modifications on biological activity of SVPH counterstructure. The biological activity of a SVPH counterstructure protein thus can be ascertained before it is used in a research study, for example.

Delivery Agents

The polypeptides also find use as carriers for delivering agents attached thereto to cells bearing SVPH counterstructures. The polypeptides thus can be used to deliver diagnostic or therapeutic agents to such cells (or to other cell types found to express SVPH counterstructures on the cell surface) in in vitro or in vivo procedures.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}I$, $^{131}I$, $^{99m}Tc$, $^{111}In$, and $^{76}Br$. Examples of radionuclides suitable for therapeutic use are $^{131}I$, $^{211}At$, $^{77}Br$, $^{186}Re$, $^{188}Re$, $^{212}Pb$, $^{212}Bi$, $^{109}Pd$, $^{64}Cu$, and $^{67}Cu$.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Detergent Additive

SVPH3-13 and 3-17 proteinases can be used as detergent additives for the removal of stains having a protein component, similar to the use of proteases described in U.S. Pat. Nos. 5,599,400 and 5,650,315. The detergent composition can contain other known detergent constituents, such as surfactants, foam enhancers, fillers, enzyme stabilizers, chlorine bleach scavengers, other proteolytic enzymes, bacteriocides, dyes, perfumes, diluents, solvents, and other conventional ingredients. The detergent composition preferably contains between 001% to 10% SVPH3-13 or 3-17 proteinase. SVPH3-13 or 3-17 proteinase can be included in a detergent composition or can be combined with other constituents at the time of use as an additive. The detergent additive can be formulated as a liquid, powder, granulate, slurry, or other conventional form of a detergent additive.

Therapeutic Agents

Polypeptides of the invention may be used in developing treatments for any disorder mediated (directly or indirectly) by defective, or insufficient amounts of the polypeptides. These polypeptides may be administered to a mammal afflicted with such a disorder.

The polypeptides may also be employed in inhibiting a biological activity of SVPH counterstructures, in in vitro or in vivo procedures. For example, a purified polypeptide may be used to inhibit SVPH counterstructures activity. Biological effects that result from the binding of SVPH counterstructures to endogenous receptors thus are inhibited.

In addition, SVPH3-13 or SVPH3-17 polypeptides may be administered to a mammal to treat a SVPH counterstructure-mediated disorder. Such SVPH counterstructure-mediated disorders include conditions caused (directly or indirectly) or exacerbated by SVPH counterstructure.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble SVPH3-13 or SVPH3-17 polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Research Agents

Another use of the polypeptide of the present invention is as a research tool for studying the biological effects that result from inhibiting SVPH3-13 or SVPH3-17 polypeptides/SVPH3-13 or SVPH3-17 polypeptide counterstructure interactions on different cell types. Polypeptides also may be employed in in vitro assays for detecting SVPH3-13 or SVPH3-17 polypeptides or SVPH counterstructures or the interactions thereof.

The interaction between SVPH3-13 (or 3-17) and its counter-structure enables screening for small molecules that interfere with the SVPH3-13 (or 3-17)/SVPH3-13 (or 3-17) counter-structure association and inhibit activity of SVPH3-13 (or 3-17) or its counter-structure. For example, the yeast two-hybrid system developed at SUNY (described in U.S. Pat. No. 5,283,173 to Fields et al.) can be used to screen for inhibitors of SVPH3-13 and 3-17 as follows. SVPH3-13 (or 3-17) and its counter-structure, or portions thereof responsible for their interaction, can be fused to the Gal4 DNA binding domain and Gal 4 transcriptional activation domain, respectively, and introduced into a strain that depends on Gal4 activity for growth on plates lacking histidine. Compounds that prevent growth can be screened in order to identify SVPH inhibitors. Alternatively, the screen can be modified so that SVPH3-13 (or 3-17)/SVPH3-13 (or 3-17) counter-structure interaction inhibits growth, so that inhibition of the interaction allows growth to occur. Another in vitro approach to screening for SVPH3-13 and 3-17 inhibition would be to immobilize one of the components (either SVPH3-13 (or 3-17) or its counter-structure) in wells of a microtiter plate, and to couple an easily detected indicator to the other component. An inhibitor of the interaction is identified by the absence of the detectable indicator from the well.

SVPH3-13 and 3-17 DNAs, SVPH3-13 and 3-17 polypeptides, and antibodies against SVPH3-13 and 3-17 polypeptides can be used as reagents in a variety of research protocols. A sample of such research protocols are given in Sambrook et al. *Molecular Cloning: A Laboratory Manual,* 2ed. Vol. 1-3, Cold Spring Harbor Laboratory Press, (1989). For example, these reagents can serve as markers for cell specific or tissue specific expression of RNA or proteins.

Similarly, these reagents can be used to investigate constitutive and transient expression of SVPH3-13 (ADAM22) or 3-17 (ADAM23) RNA or polypeptides. SVPH3-13 (ADAM22) and 3-17 (ADAM23) DNAs can be used to determine the chromosomal location of SVPH3-13 and 3-17 DNAs and to map genes in relation to this chromosomal location. SVPH3-13 and 3-17 DNAs can also be used to examine genetic heterogeneity and heredity through the use of techniques such as genetic fingerprinting, as well as to identify risks associated with genetic disorders. SVPH3-13 and 3-17 DNAs can be further used to identify additional genes related to SVPH3-13 or 3-17 DNAs and to establish evolutionary trees based on the comparison of sequences. SVPH3-13 and 3-17 DNAs and polypeptides can be used to select for those genes or proteins that are homologous to SVPH3-13 or 3-17 DNA or polypeptides, through positive screening procedures such as Southern blotting and immunoblotting and through negative screening procedures such as subtraction.

SVPH3-13 and 3-17 proteinase activities can be used as reagents in analyses with other proteinases to compare the substrate specificity and activity of the proteinases. Chimeric proteinases can be generated by swapping fragments of SVPH3-13 or 3-17 proteinase with other proteinases. Such chimeric proteinases can be analyzed with respect to altered activity and specificity.

SVPH3-13 and 3-17 polypeptides can also be used as reagents to identify (a) any protein that SVPH3-13 or 3-17 polypeptide regulates, and (b) other proteins with which it might interact. SVPH3-13 or 3-17 polypeptides could be used by coupling recombinant protein to an affinity matrix, or by using them as a bait in the 2-hybrid system.

The purified SVPH3-13 and 3-17 polypeptides according to the invention will facilitate the discovery of inhibitors of SVPH3-13 and 3-17 polypeptides. The use of a purified SVPH3-13 or 3-17 polypeptide in the screening of potential inhibitors thereof is important and can eliminate or reduce the possibility of interfering reactions with contaminants.

In addition, SVPH3-13 and 3-17 polypeptides can be used for structure-based design of SVPH3-13 and 3-17 polypeptide-inhibitors. Such structure-based design is also known as "rational drug design." The SVPH3-13 and 3-17 polypeptides can be three-dimensionally analyzed by, for example, X-ray crystallography, nuclear magnetic resonance or homology modeling, all of which are well-known methods. The use of SVPH3-13 and 3-17 polypeptide structural information in molecular modeling software systems to assist in inhibitor design and inhibitor-SVPH3-13 and inhibitor-SVPH3-17 polypeptide interactions is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of SVPH3-13 and 3-17 polypeptides for likely binding sites of substrates, synthesizing a new molecule that incorporates a predictive reactive site, and assaying the new molecule as described above.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238-255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44-50, 1981; T. Masaki et al., *Biochim. Biophys. Acta* 660:51-55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102-1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680-685, 1970). Conventionally, the method uses two separate lanes of a gel containing sodium dodecyl sulfate and a concentration of acrylamide between 6-20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76-77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252: 1102-1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

Thus, one preferred embodiment of the invention is the use of SVPH3-13 and 3-17 polypeptides as molecular weight markers to estimate the apparent molecular weight of a sample protein by gel electrophoresis. An isolated and purified SVPH3-13 polypeptide molecular weight marker according to the invention has a molecular weight of approximately 2,139 or 96,450 Daltons in the absence of glycosylation. An isolated and purified SVPH3-17 polypeptide molecular weight marker according to the invention has a molecular weight of approximately 91,866 Daltons in the absence of glycosylation. The use of these polypeptide molecular weight markers allows an increased accuracy in the determination of apparent molecular weight of proteins that have apparent molecular weights close to 2,139, 96,450, or 91,866 Daltons. It is understood of course that many different techniques can be used for the determination of the molecular weight of a sample protein using SVPH3-13 and 3-17 polypeptides and that this embodiment in no way limits the scope of the invention.

Another preferred embodiment of the invention is the use of SVPH3-13 and 3-17 fragmented peptide molecular weight markers, generated by chemical fragmentation of SVPH3-13 and 3-17 polypeptides, as molecular weight markers to estimate the apparent molecular weight of a sample protein by gel electrophoresis. The unique set of SVPH3-17 fragmented peptide molecular weight markers generated by treatment of SVPH3-17 polypeptide (SEQ ID NO: 4) with cyanogen bromide comprises 10 fragmented peptides of at least 10 amino acids in size. The estimated molecular weights of these fragmented peptides are shown in Table 1.

TABLE 1

| Amino Acids of SEQ ID NO: 4 | Molecular Weight in Daltons |
|---|---|
| 2-107 | 10,745 |
| 108-221 | 12,883 |
| 231-261 | 3,545 |
| 267-298 | 3,958 |
| 305-368 | 7,401 |
| 369-423 | 6,380 |
| 424-461 | 4,119 |
| 462-718 | 28,284 |
| 720-733 | 1,647 |
| 734-832 | 10,287 |

Therefore, cleavage of the SVPH3-17 polypeptide by chemical treatment with cyanogen bromide generates a unique set of SVPH3-17 fragmented peptide molecular weight markers. The unique and known amino acid sequence of these SVPH3-17 fragmented peptides allows the determination of the molecular weight of these fragmented peptide molecular weight markers. In this particular case, SVPH3-17 fragmented peptide molecular weight markers have molecular weights of approximately 10,745; 12,883; 3,545; 3,958; 7,401; 6,380; 4,119; 28,284; 1,647; and 10,287 Daltons.

In a further embodiment, the sample protein and the SVPH3-17 polypeptide can be simultaneously, but separately, treated with cyanogen bromide under conventional conditions that result in fragmentation of the sample protein and the SVPH3-17 polypeptide by specific hydrolysis on the carboxyl side of the methionine residues within the sample protein and the SVPH3-17 polypeptide. As described above, the SVPH3-17 fragmented peptide molecular weight markers generated by cleavage of the SVPH3-17 polypeptide with cyanogen bromide have molecular weights of approximately 10,745; 12,883; 3,545; 3,958; 7,401; 6,380; 4,119; 28,284; 1,647; and 10,287 Daltons.

The unique set of SVPH3-13 fragmented peptide molecular weight markers generated by treatment of SVPH3-13 polypeptide (SEQ ID NO:6) (alone or with a sample protein) with cyanogen bromide comprises 12 fragmented peptides of at least 10 amino acids in size. The estimated molecular weights of these fragmented peptides are shown in Table 2.

TABLE 2

| Amino Acids of SEQ ID NO: 6 | Molecular Weight in Daltons |
| --- | --- |
| 1-121 | 13,587 |
| 122-205 | 10,315 |
| 213-233 | 2,460 |
| 234-251 | 2,091 |
| 252-274 | 2,727 |
| 275-327 | 5,760 |
| 328-364 | 3,951 |
| 365-460 | 10,437 |
| 461-491 | 3,340 |
| 492-622 | 14,440 |
| 624-845 | 24,009 |
| 846-868 | 2,562 |

Therefore, cleavage of the SVPH3-13 polypeptide by chemical treatment with cyanogen bromide generates a unique set of SVPH3-13 fragmented peptide molecular weight markers. The unique and known amino acid sequence of these SVPH3-13 fragmented peptides allows the determination of the molecular weight of these fragmented peptide molecular weight markers. In this particular case, SVPH3-13 fragmented peptide molecular weight markers have molecular weights of approximately 13,587; 10,315; 2,460; 2,091; 2,727; 5,760; 3,951; 10,437; 3,340; 14,440; 24,009; and 2,562 Daltons.

In yet another embodiment, the extent of fragmentation of the SVPH3-13 and 3-17 polypeptides are further used as a control to determine the conditions expected for complete fragmentation of the sample protein. It is understood of course that many chemicals could be used to fragment SVPH3-13 and 3-17 polypeptides and that this embodiment in no way limits the scope of the invention.

In another embodiment, unique sets of SVPH3-13 and 3-17 fragmented peptide molecular weight markers can be generated from SVPH3-13 and 3-17 polypeptides using enzymes that cleave the polypeptides at specific amino acid residues. Due to the unique nature of the amino acid sequence of the SVPH3-13 and 3-17 polypeptides, cleavage at different amino acid residues will result in the generation of different sets of fragmented peptide molecular weight markers.

For example, an isolated and purified SVPH3-17 polypeptide can be treated with *Achromobacter* protease I under conventional conditions that result in fragmentation of the SVPH3-17 polypeptide by specific hydrolysis on the carboxyl side of the lysine residues within the SVPH3-17 polypeptide (T. Masaki et al., *Biochim. Biophys. Acta* 660: 44-50, 1981; T. Masaki et al., *Biochim. Biophys. Acta* 660: 51-55, 1981). Due to the unique amino acid sequence of the SVPH3-17 polypeptide, the fragmentation of SVPH3-17 polypeptide molecular weight markers with *Achromobacter* protease I generates a unique set of SVPH3-17 fragmented peptide molecular weight markers. The distribution of lysine residues determines the number of amino acids in each peptide and the unique amino acid composition of each peptide determines its molecular weight.

The unique set of SVPH3-17 fragmented peptide molecular weight markers generated by treatment of SVPH3-17 polypeptide with *Achromobacter* protease I comprises 29 fragmented peptides of at least 10 amino acids in size. The generation of 29 fragmented peptides with this enzyme treatment of the SVPH3-17 polypeptide, compared to 10 fragmented peptides with cyanogen bromide treatment of the SVPH3-17 polypeptide, clearly illustrates that both the size and number of the fragmented peptide molecular weight markers will vary depending upon the fragmentation treatment utilized to fragment the SVPH3-17 polypeptide. Both the size and number of these fragments are dictated by the amino acid sequence of the SVPH3-17 polypeptide. The estimated molecular weights of these fragmented peptides are shown in Table 3.

TABLE 3

| Amino Acids of SEQ ID NO: 4 | Molecular Weight in Daltons |
| --- | --- |
| 3-81 | 7,851 |
| 82-109 | 3,040 |
| 110-135 | 3,093 |
| 145-161 | 1,802 |
| 162-186 | 2,878 |
| 192-206 | 2,265 |
| 210-241 | 3,651 |
| 242-251 | 1,135 |
| 263-282 | 2,490 |
| 286-299 | 1,632 |
| 300-310 | 1,373 |
| 315-327 | 1,505 |
| 328-338 | 1,235 |
| 339-356 | 2,114 |
| 357-374 | 2,115 |
| 381-397 | 2,021 |
| 398-447 | 5,382 |
| 450-471 | 2,413 |
| 475-498 | 2,743 |
| 499-530 | 3,503 |
| 532-586 | 5,911 |
| 587-605 | 2,149 |
| 606-618 | 1,611 |
| 643-652 | 1,206 |
| 653-724 | 7,880 |
| 725-741 | 1,849 |
| 744-781 | 4,087 |
| 787-817 | 2,923 |
| 822-832 | 1,313 |

Therefore, cleavage of the SVPH3-17 polypeptide by enzymatic treatment with *Achromobacter* protease I generates a unique set of SVPH3-17 fragmented peptide molecular weight markers. The unique and known amino acid sequence of these fragmented peptides allows the determination of the molecular weight of these SVPH3-17 fragmented peptide molecular weight markers. In this particular case, these SVPH3-17 fragmented peptide molecular weight markers have molecular weights of approximately 7,851; 3,040; 3,093; 1,802; 2,878; 2,265; 3,651; 1,135; 2,490; 1,632; 1,373; 1,505; 1,235; 2,114; 2,115; 2,021; 5,382; 2,413; 2,743; 3,503; 5,911; 2,149 ;1,611 ;1,206; 7,880; 1,849; 4,087; 2,923; and 1,313 Daltons.

In another embodiment, the sample protein and the SVPH3-17 polypeptide can be simultaneously, but separately, treated with *Achromobacter* protease I under conventional conditions that result in fragmentation of the sample protein and the SVPH3-17 polypeptide by specific hydrolysis on the carboxyl side of the lysine residues within the sample protein and the SVPH3-17 polypeptide. The extent of fragmentation of the SVPH3-17 polypeptide is further used as a control to determine the conditions expected for complete fragmentation of the sample protein. It is understood of course that many enzymes could be used to fragment SVPH3-13 and 3-17 polypeptides and that this embodiment in no way limits the scope of the invention.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA 90:5011-5015, 1993; D. Fenyo et al., Electrophoresis 19:998-1005, 1998). A variety of computer software programs to facilitate these comparisons are accessible via the Internet, such as Protein Prospector (prospector.uscf.edu), MultiIdent (expasy.ch/sprot/multiident), PeptideSearch (mann.embl-heiedelberg.de.deSearch/FR_PeptideSearch Form), and ProFound (chait-sgi.rockefeller.edu/cgi-bin/prot-id-frag). These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976-989 (1994); M. Mann and M. Wilm, *Anal. Chem.* 66:4390-4399 (1994); J. A. Taylor and R. S. Johnson, *Rapid Comm. Mass Spec.* 11:1067-1075 (1997)). Searching programs that can be used in this process exist on the Internet, such as Lutefisk 97 (sbc.com:70/Lutefisk97), and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. In this aspect of the invention, the polypeptides based on the amino acid sequence of the SVPHs of the invention can be utilized to prepare antibodies that specifically bind to SVPH. Such antibodies specifically bind to the polypeptides via the antigen-binding sites of the antibody (as opposed to non-specific binding). Thus, the polypeptides, fragments, variants, fusion proteins, etc., as set forth above may be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques as described below.

The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind with a $K_a$ of greater than or equal to about $10^7$ $M^{-1}$. Affinities of binding partners or antibodies can be readily determined using conventional techniques, for example those described by Scatchard et al., *Ann. N.Y. Acad. Sci.,* 51:660 (1949).

Polyclonal antibodies can be readily generated from a variety of sources, for example, horses, cows, goats, sheep, dogs, chickens, rabbits, mice, or rats, using procedures that are well known in the art. In general, the purified SVPHs of the invention is administered to the host animal typically through parenteral injection. The immunogenicity of the polypeptide can be enhanced through the use of an adjuvant, for example, Freund's complete or incomplete adjuvant. Following booster immunizations, small samples of serum are collected and tested for reactivity to the polypeptide. Examples of various assays useful for such determination include those described in *Antibodies: A Laboratory Manual*, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376, 110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice, are injected intraperitoneally at least once and preferably at least twice at about 3 week intervals with isolated and purified polypeptide, optionally in the presence of adjuvant. Mouse sera are then assayed by conventional dot blot technique or antibody capture (ABC) to determine which animal is best to fuse. Approximately two to three weeks later, the mice are given an intravenous boost of polypeptide or conjugated peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig, Following washes, a label, such as $^{125}$I-polypeptide, is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569, 825 and 5,545,806 and related patents claiming priority therefrom, all of which are incorporated by reference herein.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to SVPH counterstructures may be used to inhibit a biological activity that results from such binding, such as proteolysis by SVPH3-13 or SVPH3-17. Such blocking antibodies may be identified using any suitable assay procedure, such as by testing antibodies for the ability to inhibit binding SVPH3-13 or SVPH3-17 to certain cells expressing SVPH counterstructures. Alternatively, blocking antibodies may be identified in assays for the ability to inhibit a biological effect that results from such binding, such as proteolysis by SVPH3-13 or SVPH3-17.

Such an antibody may be employed in an in vitro procedure, or administered in vivo to inhibit a biological activity mediated by the entity that generated the antibody. Disorders caused or exacerbated (directly or indirectly) by the interaction of SVPH3-13 or SVPH3-17 or SVPH counterstructures thus may be treated. A therapeutic method involves in vivo administration of a blocking antibody to a mammal in an amount effective in inhibiting a SVPH counterstructure-mediated biological activity. Monoclonal antibodies are generally preferred for use in such therapeutic methods. In one embodiment, an antigen-binding antibody fragment is employed.

Compositions comprising an antibody that is directed against SVPH3-13 or SVPH3-17 polypeptides, and a physiologically acceptable diluent, excipient, or carrier, are provided herein. Suitable components of such compositions are as described above for compositions containing SVPH3-13 or SVPH3-17 proteins.

Also provided herein are conjugates comprising a detectable (e.g., diagnostic) or therapeutic agent, attached to the antibody. Examples of such agents are presented above. The conjugates find use in in vitro or in vivo procedures.

The specification is most thoroughly understood in light of the teachings of the references cited within the specification which are hereby incorporated by reference. The embodiments within the specification and the Examples provide an illustration of embodiments of the invention and should not be construed to limit the scope of the invention. The skilled artisan readily recognizes that many other embodiments are encompassed by the invention. The following examples are provided to further illustrate particular embodiments of the invention, and are not to be construed as limiting the scope of the present invention.

EXAMPLE 1

RNA Expression of SVPH3-13 and SVPH3-17

Figure 2:
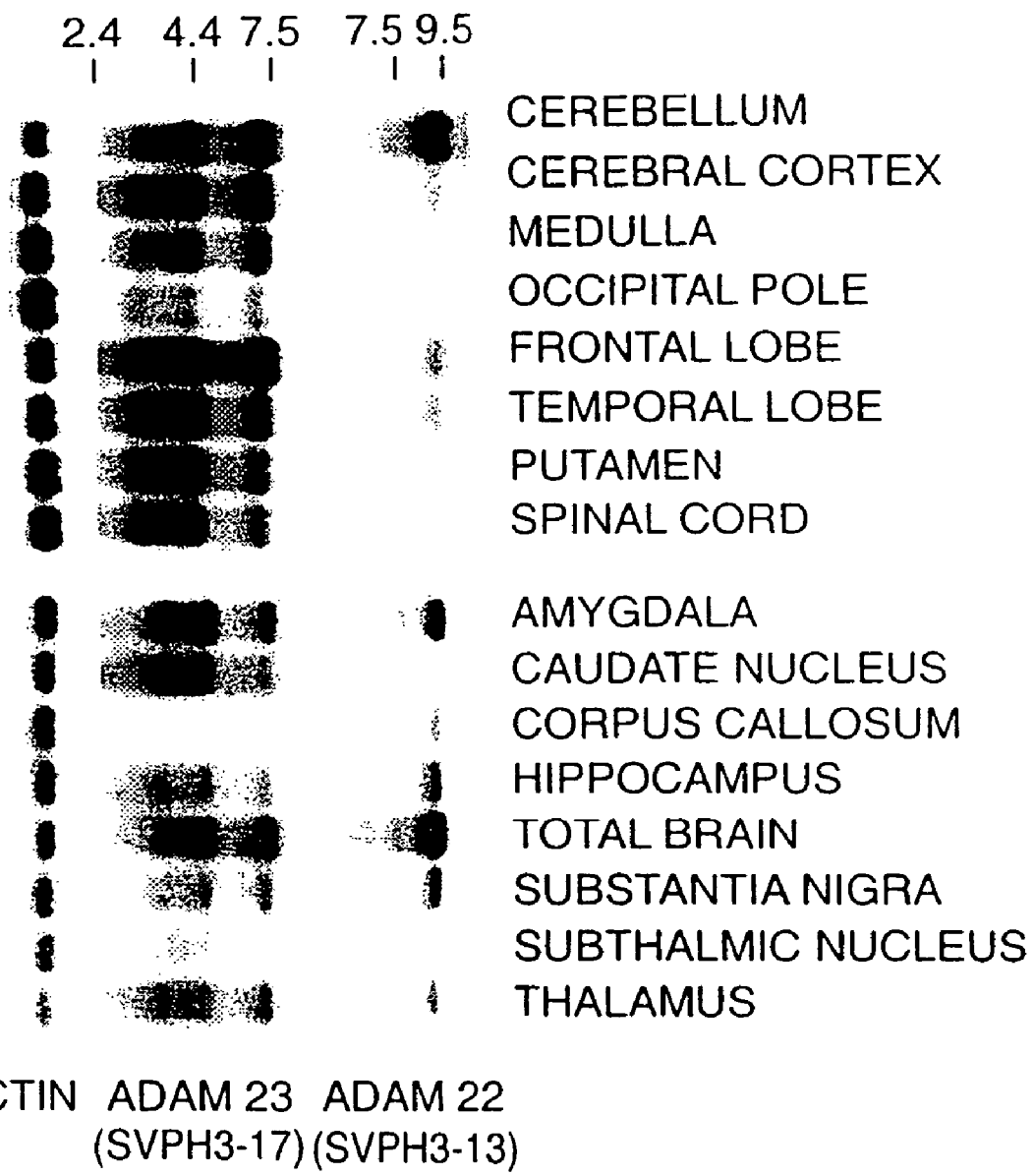
FIG. 2 presents expression data of SVPH3-13 and SVPH3-17 RNA in brain-associated tissues by Northern blot.

Northern blots were purchased from Clontech (catalog numbers 7760-1, 7759-01, 7755-1, and 7750-1). The blots were prehybridized in Stark's buffer (50% formamide, 50mM $KPO_4$, 5×SSC, 1% SDS, 5× Denhardt's solution, 0.05% sarkosyl, and 300 μg/ml salmon sperm DNA) at 63° C. for at least 1 hour, and then incubated at 63° C. overnight in Stark's buffer using $^{32}$P-labeled SVPH3-13 or SVPH3-17 riboprobes (Cosman et al., 1984). Blots were then washed sequentially to high stringency (0.1×SSC, 0.1%SDS at 63° C.) and exposed to film (X-OMAT AR, Eastman Kodak Co., Rochester, N.Y.). Exposed films were developed in an automated x-ray film processor. SVPH3-17 (ADAM23) and SVPH3-13 (ADAM22) antisense riboprobes were prepared by in vitro transcription from a T7 RNA promoter with a commercially available kit (MAXIscript, Ambion, Inc., Austin, Tex.) using ($\alpha$-$^{32}$P)UTP as the labeled nucleotide. The results are shown in FIGS. 1 and 2.

EXAMPLE 2

Radiation-Hybrid Mapping of SVPH3-13 and SVPH3-17

Chromosomal mapping of SVPH3-13 and SVPH3-17 was performed by radiation-hybrid mapping (Walter et al., 1994). The GeneBridge 4 radiation-hybrid mapping panel (Research Genetics, Huntsville, Ala.) was screened with specific primer pairs for SVPH3-13 (ADAM22) and SVPH3-17 (ADAM23).

The primers used for PCR screening of SVPH3-13 were: 5'-TATCTTCCTAAAAAGTTCACCCAGTGTAATATTG-3' (sense)(SEQ ID NO:7) and 5'-TGCTTTCTATTCCCAT-CAGAATAGCCC-3' (antisense)(SEQ ID NO:8). These primers generated a product of 298 base pairs.

The primers used for PCR screening of SVPH3-17 were: 5'-CTTTTTACAGAGAGGAGGTGGAG-3' (sense)(SEQ ID NO:9) and 5'-GAAACACCAGAGACTGAGAATGC-3' (antisense)(SEQ ID NO:10). These primers generated a product of 263 base pairs.

Data from two independent PCR screenings were scored against STS markers from the Whitehead Institute/MIT Center for Genome Research database using the statistical program RHMAPPER.

---

What is claimed is:

1. An isolated polypeptide having disintegrin activity and comprising an amino acid sequence selected from the group consisting of:
   (a) an amino acid sequence at least 95% identical to the sequence of amino acids from position 496 through position 599 of SEQ ID NO:4;
   (b) an amino acid sequence at least 95% identical to the sequence of amino acids from position 532 through 586 of SEQ ID NO:4; and
   (c) an amino acid sequence having at least 95% amino acid identity to SEQ ID NO:4.

2. A fusion protein comprising a polypeptide of claim 1 and a heterologous polypeptide.

3. The fusion protein of claim 2, wherein the heterologous polypeptide is selected from the group consisting of an Fc polypeptide, a peptide linker, and/or a leucine zipper polypeptide.

4. An isolated polypeptide having disintegrin activity and expressed according to a method comprising culturing a host cell containing a recombinant vector comprising a nucleic acid molecule encoding said polypeptide having disintegrin activity under conditions promoting expression of said recombinant vector, wherein said polypeptide-encoding nucleic acid molecule comprised by said recombinant vector is selected from the group consisting of:
   (a) a nucleic acid molecule having at least 95% identity to the sequence of SEQ ID NO:2;
   (b) a nucleic acid molecule encoding an amino acid sequence having at least 95% identity to the sequence of SEQ ID NO:4; and
   (c) a nucleic acid molecule encoding a polypeptide having disintegrin activity and having at least 95% identity to the sequence of amino acids from position 532 through position 586 of SEQ ID NO:4.

5. The polypeptide of claim 4 in non-glycosylated form.

* * * * *